United States Patent
Hansmann et al.

(10) Patent No.: US 6,979,293 B2
(45) Date of Patent: Dec. 27, 2005

(54) BLOOD FLOW REESTABLISHMENT DETERMINATION

(75) Inventors: Douglas R. Hansmann, Bainbridge Island, WA (US); Robert L. Wilcox, Bothell, WA (US); Floyd Karp, Seattle, WA (US); Natalya Peskin, Redmond, WA (US); Kim R. Volz, Duvall, WA (US)

(73) Assignee: Ekos Corporation, Bothell, WA (US)

( * ) Notice: Subject to any disclaimer, the term of this patent is extended or adjusted under 35 U.S.C. 154(b) by 272 days.

(21) Appl. No.: 10/320,847

(22) Filed: Dec. 16, 2002

(65) Prior Publication Data

US 2003/0220568 A1    Nov. 27, 2003

Related U.S. Application Data

(60) Provisional application No. 60/341,430, filed on Dec. 14, 2001, provisional application No. 60/347,350, filed on Jan. 10, 2002, provisional application No. 60/369,453, filed on Apr. 2, 2002.

(51) Int. Cl.⁷ ................................................ A61B 8/00
(52) U.S. Cl. ........................ 600/439; 600/467; 601/2; 601/3
(58) Field of Search ...................... 601/2–4; 600/439; 606/128, 169; 604/22

(56) References Cited

U.S. PATENT DOCUMENTS

| | | | |
|---|---|---|---|
| 5,158,071 A | 10/1992 | Umemura et al. | |
| 5,197,946 A | 3/1993 | Tachibana | |
| 5,269,291 A | 12/1993 | Carter | |
| 5,318,014 A | 6/1994 | Carter | |
| 5,351,693 A | 10/1994 | Taimisto et al. | |
| 5,362,309 A | 11/1994 | Carter | |
| 5,368,036 A | 11/1994 | Tanaka et al. | |
| 5,372,138 A * | 12/1994 | Crowley et al. ............. | 600/463 |
| 5,380,273 A | 1/1995 | Dubrul et al. | |
| 5,431,663 A | 7/1995 | Carter | |
| 5,447,509 A | 9/1995 | Mills et al. | |
| 5,453,575 A | 9/1995 | O'Donnell et al. | |
| 5,474,531 A | 12/1995 | Carter | |
| 5,588,432 A | 12/1996 | Crowley | |
| 5,620,479 A | 4/1997 | Diederich | |
| 5,628,728 A | 5/1997 | Tachibana et al. | |
| 5,630,837 A | 5/1997 | Crowley | |
| 5,713,848 A | 2/1998 | Dubrul et al. | |
| 5,735,811 A | 4/1998 | Brisken | |
| 5,916,192 A | 6/1999 | Nita et al. | |
| 5,935,124 A | 8/1999 | Klumb et al. | |

(Continued)

FOREIGN PATENT DOCUMENTS

JP    H02-180275    7/1990

(Continued)

Primary Examiner—Ali Imam
(74) Attorney, Agent, or Firm—Knobbe, Martens, Olson & Bear LLP

(57) ABSTRACT

A method for monitoring a clot dissolution treatment in a patient's vasculature comprises positioning a catheter at a treatment site in the patient's vasculature. The method further comprises performing a clot dissolution treatment at the treatment site. The clot dissolution treatment comprises delivering ultrasonic energy and a therapeutic compound from the catheter to the treatment site such that a clot located at the treatment site at least partially dissolves. The method further comprises delivering a thermal measurement signal from a first portion of the catheter to the treatment site during the clot dissolution treatment. The method further comprises receiving the thermal measurement signal at a second portion of the catheter. The method further comprises comparing the delivered thermal measurement signal with the received thermal measurement signal to evaluate a blood flow rate at the treatment site.

37 Claims, 17 Drawing Sheets

U.S. PATENT DOCUMENTS

| | | |
|---|---|---|
| 5,997,497 A | 12/1999 | Nita et al. |
| 6,001,069 A | 12/1999 | Tachibana et al. |
| 6,024,718 A | 2/2000 | Chen et al. |
| 6,096,000 A | 8/2000 | Tachibana et al. |
| 6,110,098 A | 8/2000 | Renirie et al. |
| 6,113,558 A * | 9/2000 | Rosenschein et al. ......... 601/2 |
| 6,135,971 A | 10/2000 | Hutchinson et al. |
| 6,176,842 B1 | 1/2001 | Tachibana et al. |
| 6,196,973 B1 | 3/2001 | Lazenby et al. |
| 6,210,356 B1 | 4/2001 | Anderson et al. |
| 6,221,038 B1 | 4/2001 | Brisken |
| 6,228,046 B1 | 5/2001 | Brisken |
| 6,231,516 B1 | 5/2001 | Keilman et al. |
| 6,287,271 B1 | 9/2001 | Dubrul et al. |
| 6,296,619 B1 | 10/2001 | Brisken et al. |
| 6,361,554 B1 | 3/2002 | Brisken |
| 6,387,052 B1 | 5/2002 | Quinn et al. |
| 6,394,997 B1 | 5/2002 | Lemelson |
| 6,461,586 B1 | 10/2002 | Unger |
| 6,485,430 B1 | 11/2002 | Quinn et al. |
| 6,511,478 B1 | 1/2003 | Burnside et al. |
| 6,537,224 B2 | 3/2003 | Mauchamp et al. |
| 6,542,767 B1 | 4/2003 | McNichols et al. |
| 2002/0019644 A1 | 2/2002 | Hastings et al. |
| 2002/0068869 A1 | 6/2002 | Brisken et al. |

FOREIGN PATENT DOCUMENTS

| | | |
|---|---|---|
| WO | WO 92/07622 | 5/1992 |
| WO | WO 97/19645 | 6/1997 |
| WO | WO 98/11826 | 3/1998 |
| WO | WO 99/42039 | 8/1999 |
| WO | WO 00/00095 | 1/2000 |
| WO | WO 01/13357 | 2/2001 |
| WO | WO 01/87174 | 11/2001 |

* cited by examiner

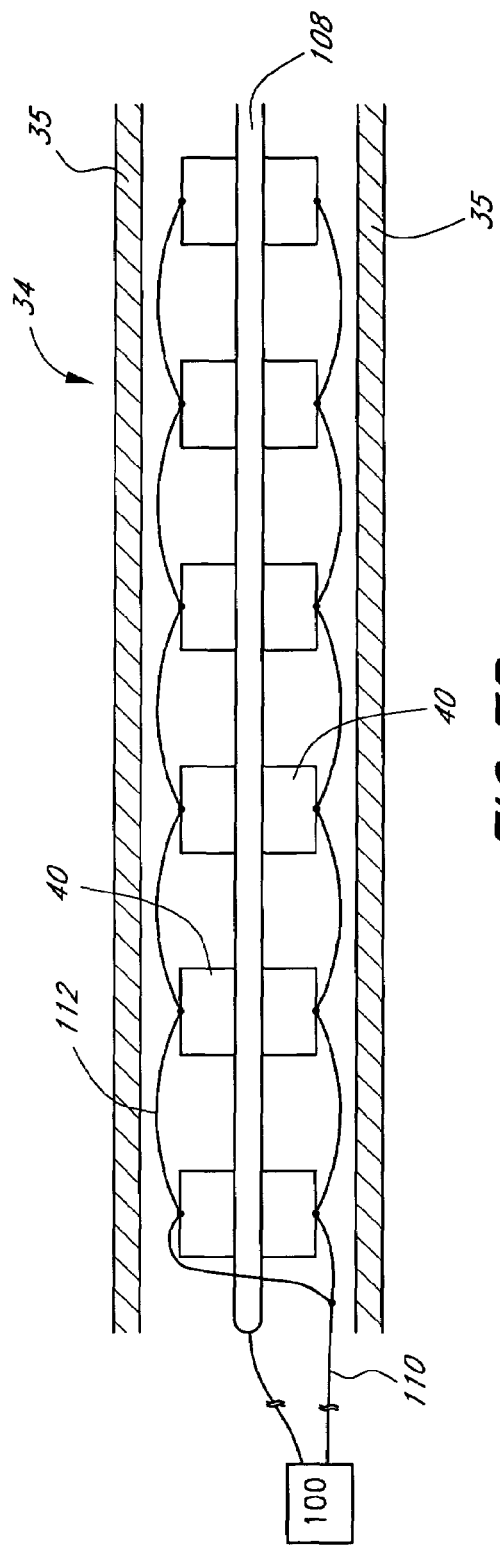
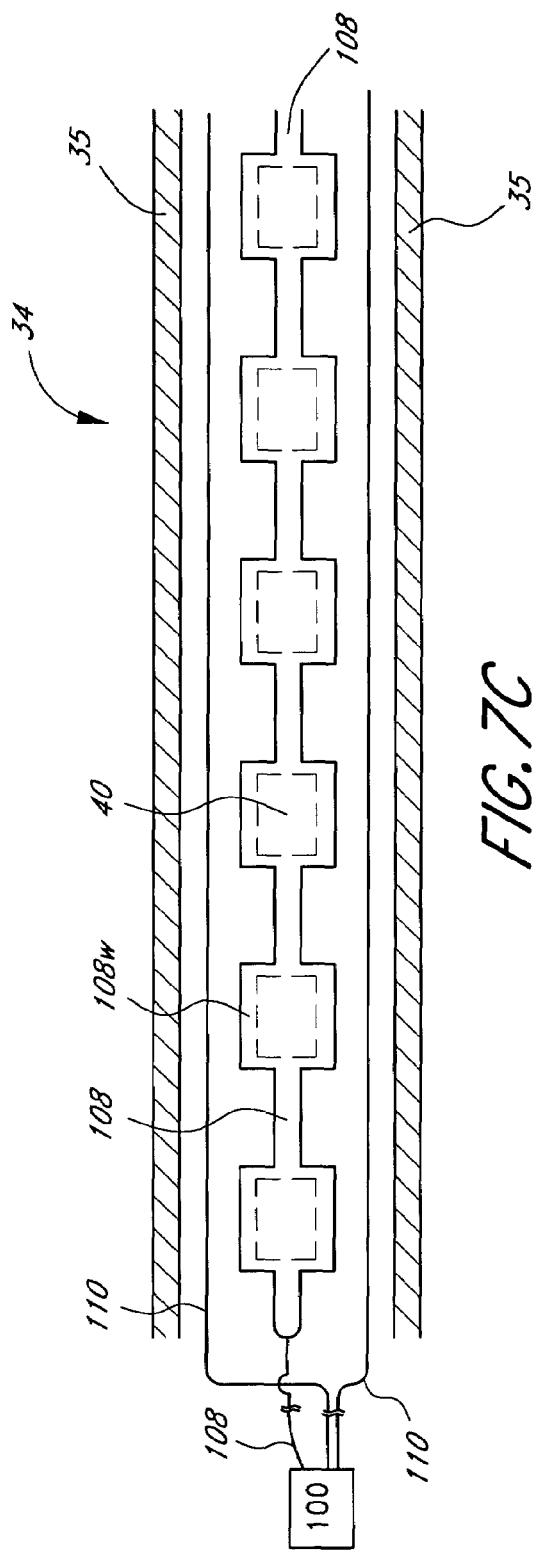

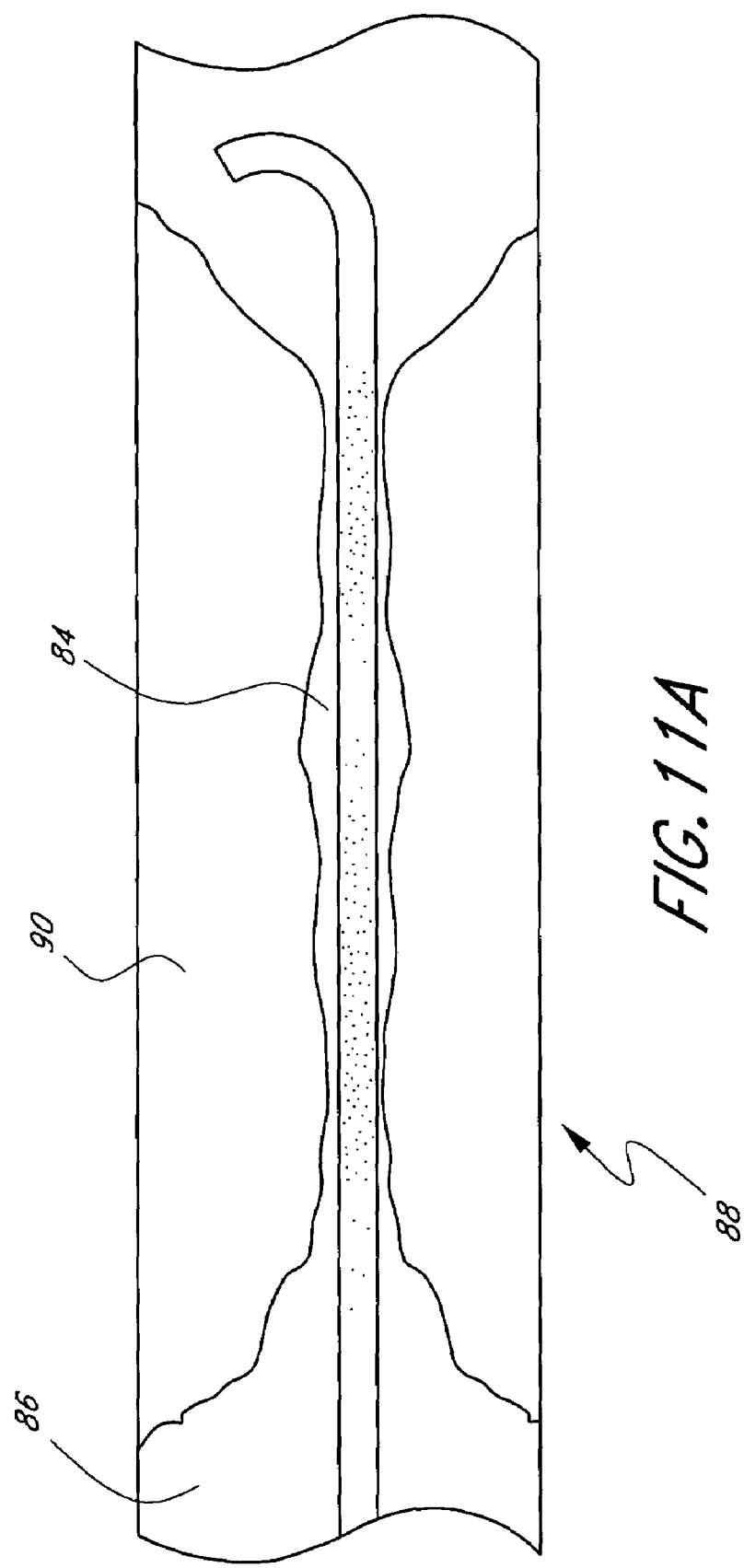

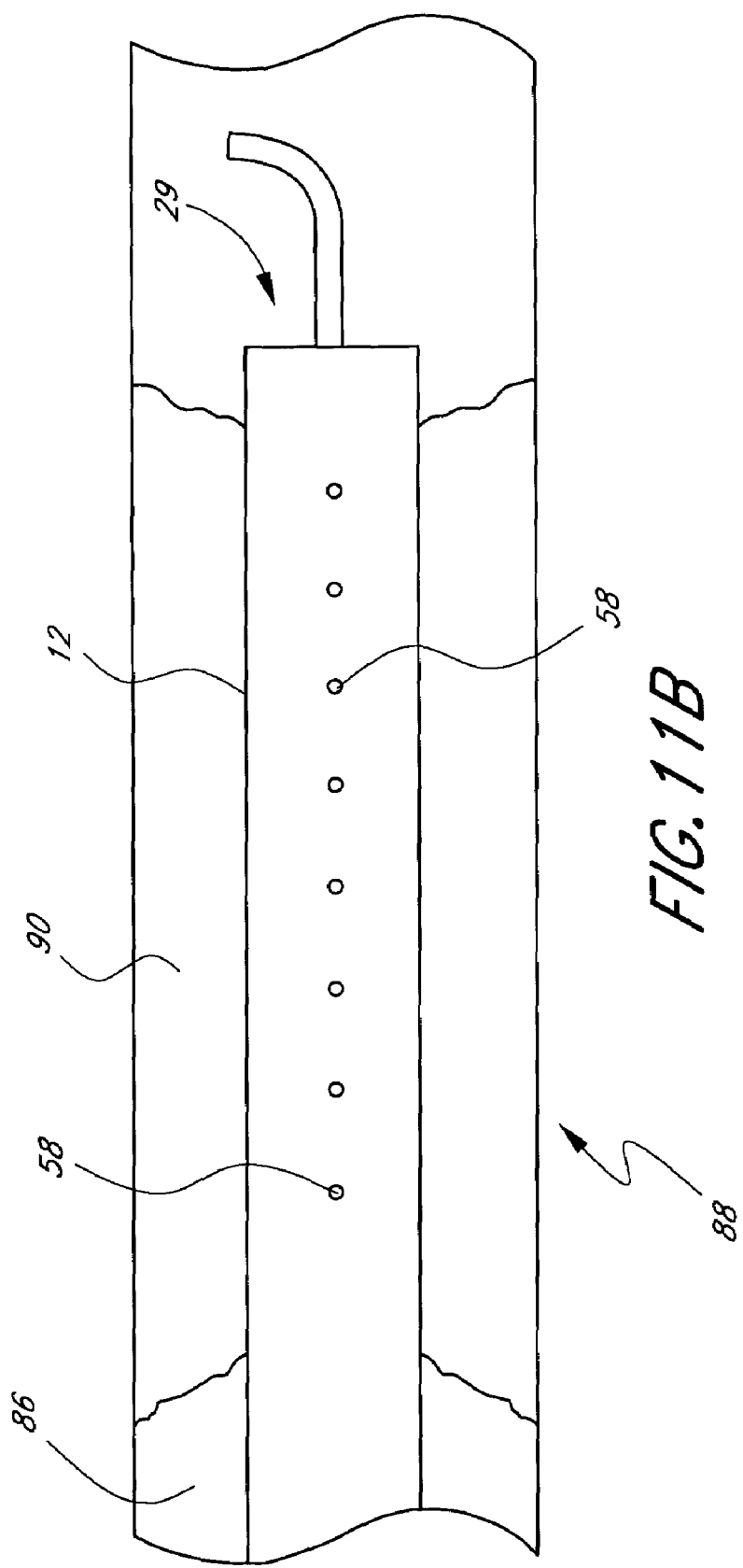

BLOOD FLOW REESTABLISHMENT DETERMINATION

PRIORITY APPLICATION

This application claims priority under 35 U.S.C. §119(e) from U.S. Provisional Patent Application Ser. No. 60/341,430, entitled "Methods and Apparatus for Determining Reestablishment of Blood Flow" and filed Dec. 14, 2001; as well as U.S. Provisional Application Ser. No. 60/347,350, entitled "Methods and Apparatus for Determining Reestablishment of Blood Flow" and filed Jan. 10, 2002; as well as U.S. Provisional Application Ser. No. 60/369,453, entitled "Methods and Apparatus for Determining Reestablishment of Blood Flow" and filed Apr. 2, 2002. The entire disclosure of all three of these priority documents is hereby incorporated by reference in its entirety.

BACKGROUND OF THE INVENTION

1. Field of the Invention

The preferred embodiments of the present invention relate to methods and apparatuses for monitoring the efficacy of a clot dissolution treatment. The methods and apparatuses are particularly well suited for use with an ultrasonic catheter configured to deliver ultrasonic energy and a therapeutic compound to a treatment site.

2. Description of the Related Art

Several medical applications use ultrasonic energy. For example, U.S. Pat. Nos. 4,821,740, 4,953,565 and 5,007,438 disclose the use of ultrasonic energy to enhance the effect of various therapeutic compounds. An ultrasonic catheter can be used to deliver ultrasonic energy and a therapeutic compound to a treatment site in a patient's body. Such an ultrasonic catheter typically includes an ultrasound assembly configured to generate ultrasonic energy and a fluid delivery lumen for delivering the therapeutic compound to the treatment site.

As taught in U.S. Pat. No. 6,001,069, such ultrasonic catheters can be used to treat human blood vessels that have become partially or completely occluded by plaque, thrombi, emboli or other substances that reduce the blood carrying capacity of the vessel. To remove or reduce the occlusion, the ultrasonic catheter is used to deliver solutions containing dissolution compounds directly to the occlusion site. Ultrasonic energy generated by the ultrasound assembly enhances the therapeutic effect of the dissolution compounds. For example, in one application of such an ultrasonic catheter, an ultrasound-enhanced thrombolytic therapy dissolves blood clots in arteries and veins in the treatment of diseases such as peripheral arterial occlusion or deep vein thrombosis. In such applications, ultrasonic energy enhances thrombolysis with agents such as urokinase, tissue plasminogen activator ("TPA") and the like.

Ultrasonic catheters can also be used to enhance gene therapy at a treatment site within the patient's body. For example, U.S. Pat. No. 6,135,976 discloses an ultrasonic catheter having one or more expandable sections capable of occluding a section of a body lumen, such as a blood vessel. A gene therapy composition is then delivered to the occluded vessel through the catheter fluid delivery lumen. Ultrasonic energy generated by the ultrasound assembly is applied to the occluded vessel, thereby enhancing the delivery of a genetic composition into the cells of the occluded vessel.

Ultrasonic catheters can also be used to enhance delivery and activation of light activated drugs. For example, U.S. Pat. No. 6,176,842 discloses methods for using an ultrasonic catheter to treat biological tissues by delivering a light activated drug to the biological tissues and exposing the light activated drug to ultrasound energy.

SUMMARY OF THE INVENTION

In certain medical procedures, it is desirable to provide no more therapeutic compound or ultrasonic energy to the treatment site than necessary to perform a medical treatment. For example, certain therapeutic compounds, although effective in dissolving blockages in the vascular system, may have adverse side effects on other biological systems. In addition, certain therapeutic compounds are expensive, and thus it is desired to use such therapeutic compounds judiciously. Likewise, excess ultrasonic energy applied to patient's vasculature may have unwanted side effects. Thus, as a treatment progresses, it may be desired to reduce, and eventually terminate, the flow of therapeutic compound or the supply of ultrasonic energy to a treatment site. On the other hand, if a clot dissolution treatment is progressing too slowly, it may be desired to increase the delivery of therapeutic compound or ultrasonic energy to the treatment site in an attempt to cause the treatment to progress faster. To date, it has been difficult to monitor the progression or efficacy of a clot dissolution treatment, and therefore to adjust the flow of therapeutic compound or the delivery of ultrasonic energy to the treatment site accordingly.

Therefore, a need exists for an improved ultrasonic catheter capable of monitoring the progression or efficacy of a clot dissolution treatment. Preferably, it is possible to adjust the flow of therapeutic compound and/or the delivery of ultrasonic energy to the treatment site as the clot dissolution treatment progresses, eventually terminating the flow of therapeutic compound and the delivery of ultrasonic energy when the treatment has concluded.

As such, according to one embodiment of the present invention, a method for monitoring a clot dissolution treatment in a patient's vasculature comprises positioning a catheter at a treatment site in the patient's vasculature. The method further comprises performing a clot dissolution treatment at the treatment site. The clot dissolution treatment comprises delivering ultrasonic energy and a therapeutic compound from the catheter to the treatment site such that a clot located at the treatment site at least partially dissolves. The method further comprises delivering a thermal measurement signal from a first portion of the catheter to the treatment site during the clot dissolution treatment. The method further comprises receiving the thermal measurement signal at a second portion of the catheter. The method further comprises comparing the delivered thermal measurement signal with the received thermal measurement signal to evaluate a blood flow rate at the treatment site.

According to another embodiment of the present invention, a method comprises positioning a catheter at a treatment site in a patient's vasculature. A blockage is located at the treatment site. The method further comprises performing a medical treatment at the treatment site. The medical treatment is configured to reduce the blockage. The method further comprises making a plurality of thermal energy measurements at the treatment site while the medical treatment is being performed. The method further comprises evaluating the reduction in the blockage based on the plurality of thermal energy measurements.

According to another embodiment of the present invention, an ultrasound catheter for evaluating the efficacy of a clot dissolution treatment comprises an upstream region.

The catheter further comprises a downstream region located opposite the upstream region. The catheter further comprises a treatment zone partially extending into both the upstream region and the downstream region. The catheter further comprises an ultrasonic assembly positioned within the treatment zone. The ultrasonic assembly comprises at least one ultrasound radiating member configured to perform a clot dissolution treatment. The catheter further comprises a thermal energy source positioned in the upstream region. The thermal energy source is configured to deliver a thermal measurement signal to the treatment zone during the clot dissolution treatment. The catheter further comprises a thermal energy detector positioned in the downstream region. The thermal energy detector is configured to receive the thermal measurement signal from the treatment zone. The catheter further comprises control circuitry configured to compare the thermal measurement signal delivered from the thermal energy source to the thermal measurement signal received at the thermal energy detector.

According to another embodiment of the present invention, an apparatus comprises a catheter having an upstream region, a downstream region and a treatment zone partially extending into both the upstream region and the downstream region. The apparatus further comprises an ultrasonic assembly positioned within the treatment zone. The ultrasonic assembly comprises at least one ultrasound radiating member configured to perform a clot dissolution treatment. The apparatus further comprises a thermal energy detector positioned in the treatment zone. The thermal energy detector is configured to make a plurality of thermal energy measurements during the clot dissolution treatment. The apparatus further comprises means for measuring thermal dilution in the treatment zone during the clot dissolution treatment.

According to another embodiment of the present invention, a method comprises positioning a catheter having an ultrasound radiating member proximal to an obstruction in a patient's vasculature. The method further comprises performing an obstruction dissolution treatment by applying a therapeutic compound and ultrasonic energy to the obstruction such that the obstruction is at least partially dissolved. The method further comprises sensing an at least partial reestablishment of blood flow past the partially dissolved obstruction. The method further comprises adjusting the obstruction dissolution treatment in response to the at least partial reestablishment of blood flow.

BRIEF DESCRIPTION OF THE DRAWINGS

FIG. 7B is a cross-sectional view of the ultrasound assembly of FIG. 7A taken along line 7B—7B.

FIG. 7C is a cross-sectional view of the ultrasound assembly of FIG. 7A taken along line 7C—7C.

FIG. 11A is a side view of a treatment site.

FIG. 11B is a side view of the distal end of an ultrasonic catheter positioned at the treatment site of FIG. 11A.

DETAILED DESCRIPTION OF PREFERRED EMBODIMENTS

Figure 1:
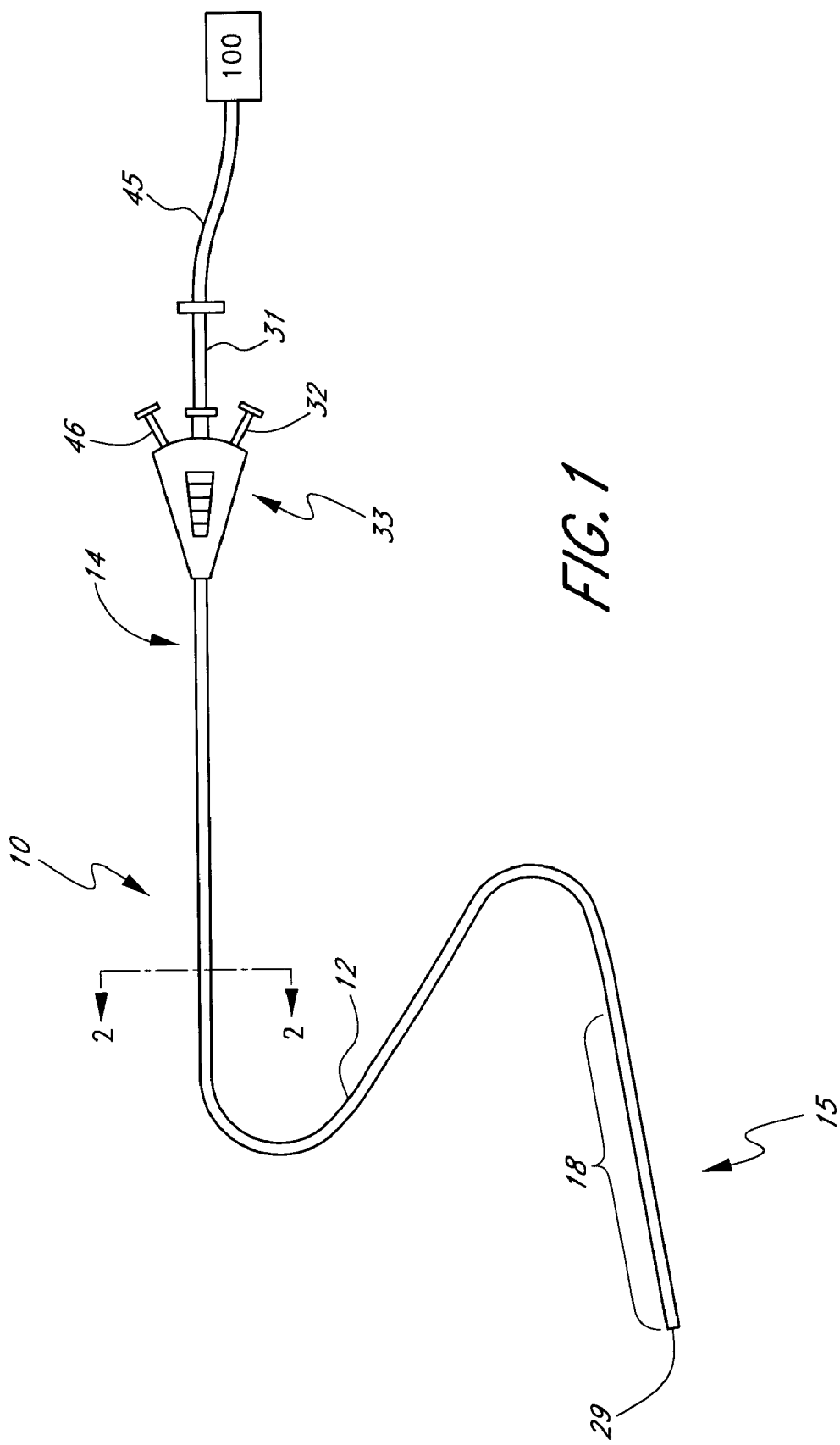
FIG. 1 is a schematic illustration of an ultrasonic catheter configured for insertion into large vessels of the human body.

As described above, it is desired to provide an ultrasonic catheter having various features and advantages. Examples of such features and advantages include the ability to monitor the progression or efficacy of a clot dissolution treatment. In another embodiments, the catheter has the ability to adjust the delivery of a therapeutic compound based on the progression of the clot dissolution treatment. Preferred embodiments of an ultrasonic catheter having certain of these features and advantages are described herein. Methods of using such an ultrasonic catheter are also described herein.

The ultrasonic catheters described herein can be used to enhance the therapeutic effects of therapeutic compounds at a treatment site within a patient's body. As used herein, the term "therapeutic compound" refers broadly, without limitation, to a drug, medicament, dissolution compound, genetic material or any other substance capable of effecting physiological functions. Additionally, any mixture comprising any such substances is encompassed within this definition of "therapeutic compound", as well as any substance falling within the ordinary meaning of these terms. The enhancement of the effects of therapeutic compounds using ultrasonic energy is described in U.S. Pat. Nos. 5,318,014, 5,362,309, 5,474,531, 5,628,728, 6,001,069 and 6,210,356, the entire disclosure of which are hereby incorporated by herein by reference. Specifically, for applications that treat human blood vessels that have become partially or completely occluded by plaque, thrombi, emboli or other substances that reduce the blood carrying capacity of a vessel, suitable therapeutic compounds include, but are not limited to, an aqueous solution containing Heparin, Uronkinase, Streptokinase, TPA and BB-10153 (manufactured by British Biotech, Oxford, UK).

Certain features and aspects of the ultrasonic catheters disclosed herein may also find utility in applications where the ultrasonic energy itself provides a therapeutic effect. Examples of such therapeutic effects include preventing or reducing stenosis and/or restenosis; tissue ablation, abrasion or disruption; promoting temporary or permanent physiological changes in intracellular or intercellular structures; and rupturing micro-balloons or micro-bubbles for therapeutic compound delivery. Further information about such methods can be found in U.S. Pat. Nos. 5,261,291 and 5,431,663, the entire disclosure of which are hereby incorporated by herein by reference. Further information about using cavitation to produce biological effects can be found in U.S. Pat. No. RE36,939.

The ultrasonic catheters described herein are configured for applying ultrasonic energy over a substantial length of a body lumen, such as, for example, the larger vessels located in the leg. However, it should be appreciated that certain features and aspects of the present invention may be applied to catheters configured to be inserted into the small cerebral vessels, in solid tissues, in duct systems and in body cavities. Such catheters are described in U.S. patent application Ser. No. 10/309,417, filed Dec. 3, 2002. Additional embodiments that may be combined with certain features and aspects of the embodiments described herein are described in U.S. patent application Ser. No. 10/291,891, filed Nov. 7, 2002, the entire disclosure of which is hereby incorporated herein by reference.

For purposes of summarizing the invention and the advantages achieved over the prior art, certain objects and advantages of the invention have been described above. It is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

Ultrasound Catheter Structure and Use

With initial reference to FIG. 1, an ultrasonic catheter 10 configured for use in the large vessels of a patient's anatomy is schematically illustrated. For example, the ultrasonic catheter 10 illustrated in FIG. 1 can be used to treat long segment peripheral arterial occlusions, such as those in the vascular system of the leg.

As illustrated in FIG. 1, the ultrasonic catheter 10 generally comprises a multi-component, elongate flexible tubular body 12 having a proximal region 14 and a distal region 15. The tubular body 12 includes a flexible energy delivery section 18 and a distal exit port 29 located in the distal region 15 of the catheter 10. A backend hub 33 is attached to the proximal region 14 of the tubular body 12, the backend hub 33 comprising a proximal access port 31, an inlet port 32 and a cooling fluid fitting 46. The proximal access port 31 can be connected to control circuitry 100 via cable 45.

The tubular body 12 and other components of the catheter 10 can be manufactured in accordance with any of a variety of techniques well known in the catheter manufacturing field. Suitable materials and dimensions can be readily selected based on the natural and anatomical dimensions of the treatment site and on the desired percutaneous access site.

For example, in a preferred embodiment the proximal region 14 of the tubular body 12 comprises a material that has sufficient flexibility, kink resistance, rigidity and structural support to push the energy delivery section 18 through the patient's vasculature to a treatment site. Examples of such materials include, but are not limited to, extruded polytetrafluoroethylene ("PTFE"), polyethylenes ("PE"), polyamides and other similar materials. In certain embodiments, the proximal region 14 of the tubular body 12 is reinforced by braiding, mesh or other constructions to provide increased kink resistance and pushability. For example, nickel titanium or stainless steel wires can be placed along or incorporated into the tubular body 12 to reduce kinking.

In an embodiment configured for treating thrombus in the arteries of the leg, the tubular body 12 has an outside diameter between about 0.060 inches and about 0.075 inches. In another embodiment, the tubular body 12 has an outside diameter of about 0.071 inches. In certain embodiments, the tubular body 12 has an axial length of approximately 105 centimeters, although other lengths may by appropriate for other applications.

The energy delivery section 18 of the tubular body 12 preferably comprises a material that is thinner than the material comprising the proximal region 14 of the tubular body 12 or a material that has a greater acoustic transparency. Thinner materials generally have greater acoustic transparency than thicker materials. Suitable materials for the energy delivery section 18 include, but are not limited to, high or low density polyethylenes, urethanes, nylons, and the like. In certain modified embodiments, the energy delivery section 18 may be formed from the same material or a material of the same thickness as the proximal region 14.

In certain embodiments, the tubular body 12 is divided into at least three sections of varying stiffness. The first section, which preferably includes the proximal region 14, has a relatively higher stiffness. The second section, which is located in an intermediate region between the proximal region 14 and the distal region 15 of the tubular body 12, has a relatively lower stiffness. This configuration further facilitates movement and placement of the catheter 10. The third section, which preferably includes the energy delivery section 18, generally has a lower stiffness than the second section.

Figure 2:
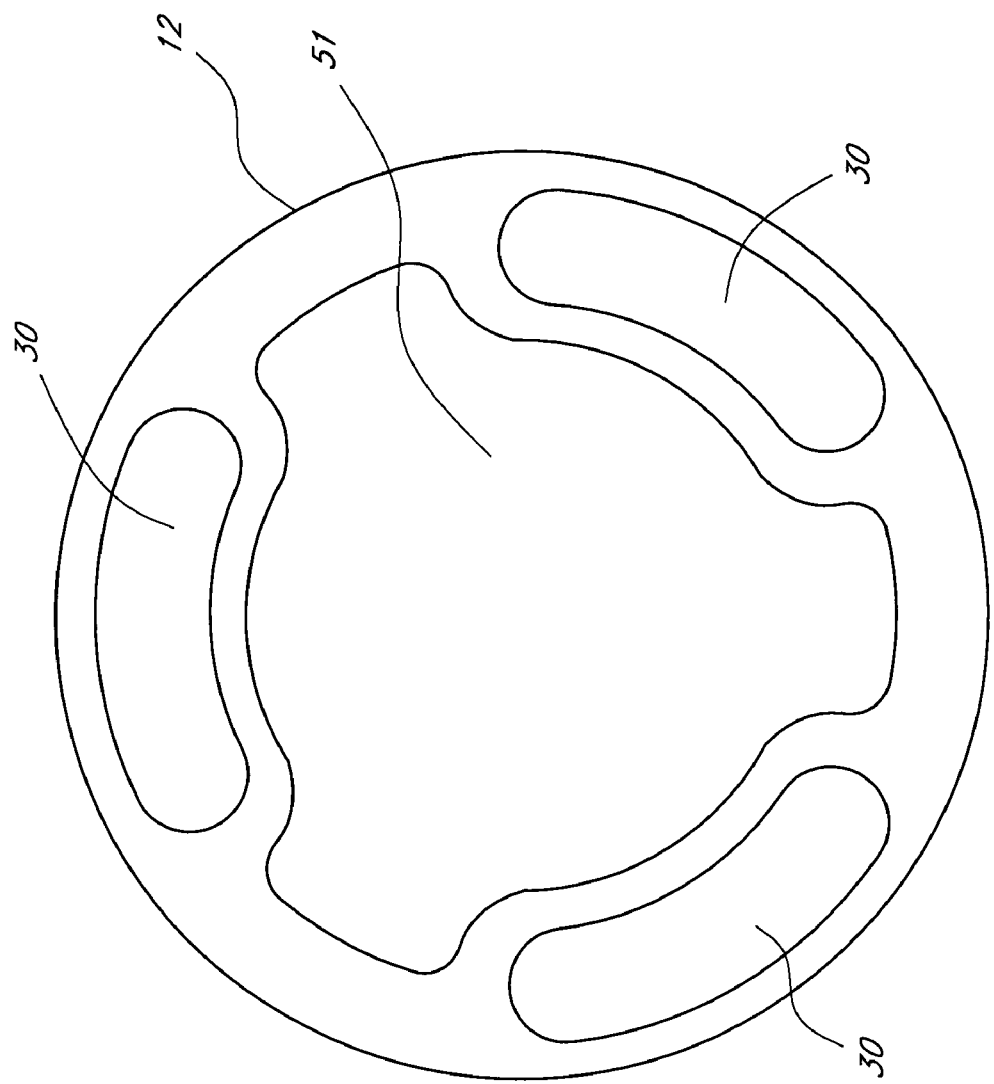
FIG. 2 is a cross-sectional view of the ultrasonic catheter of FIG. 1 taken along line 2—2.

FIG. 2 illustrates a cross section of the tubular body 12 taken along line 2—2 in FIG. 1. In the embodiment illustrated in FIG. 2, three fluid delivery lumens 30 are incorporated into the tubular body 12. In other embodiments, more or fewer fluid delivery lumens can be incorporated into the tubular body 12. The arrangement of the fluid delivery lumens 30 preferably provides a hollow central lumen 51 passing through the tubular body 12. The cross-section of the tubular body 12, as illustrated in FIG. 2, is preferably substantially constant along the length of the catheter 10. Thus, in such embodiments, substantially the same cross-section is present in both the proximal region 14 and the distal region 15 of the catheter 10, including the energy delivery section 18.

In certain embodiments, the central lumen 51 has a minimum diameter greater than about 0.030 inches. In another embodiment, the central lumen 51 has a minimum diameter greater than about 0.037 inches. In one preferred embodiment, the fluid delivery lumens 30 have dimensions of about 0.026 inches wide by about 0.0075 inches high, although other dimensions may be used in other applications.

As described above, the central lumen 51 preferably extends through the length of the tubular body 12. As illustrated in FIG. 1, the central lumen 51 preferably has a distal exit port 29 and a proximal access port 31. The proximal access port 31 forms part of the backend hub 33, which is attached to the proximal region 14 of the catheter 10. The backend hub 33 preferably further comprises cooling fluid fitting 46, which is hydraulically connected to the central lumen 51. The backend hub 33 also preferably comprises a therapeutic compound inlet port 32, which is in hydraulic connection with the fluid delivery lumens 30, and which can be hydraulically coupled to a source of therapeutic compound via a hub such as a Luer fitting.

Figure 3:
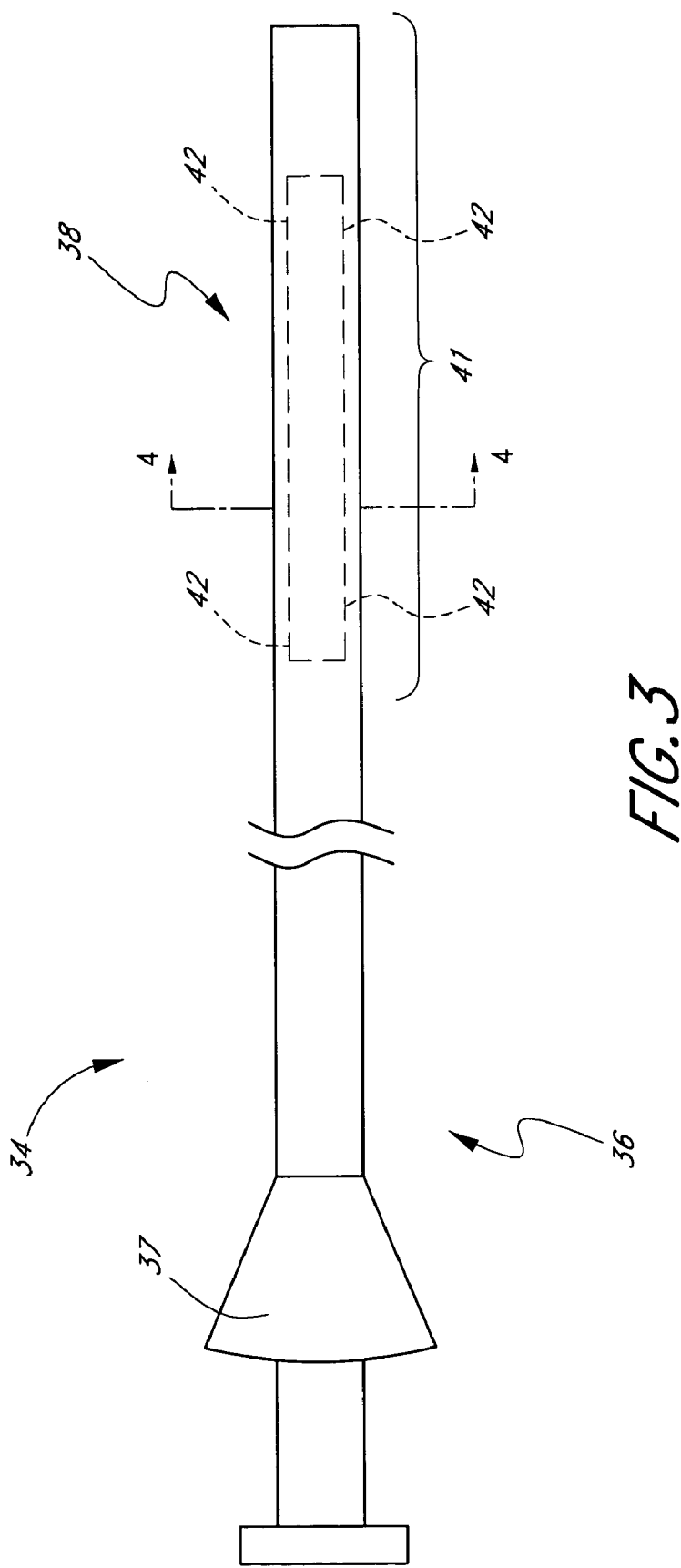
FIG. 3 is a schematic illustration of an elongate inner core configured to be positioned within the central lumen of the catheter illustrated in FIG. 2.

The central lumen 51 is configured to receive an elongate inner core 34 of which a preferred embodiment is illustrated in FIG. 3. The elongate inner core 34 preferably comprises a proximal region 36 and a distal region 38. Proximal hub 37 is fitted on the inner core 34 at one end of the proximal region 36. One or more ultrasound radiating members are positioned within an inner core energy delivery section 41 located within the distal region 38. The ultrasound radiating members form an ultrasound assembly 42, which will be described in greater detail below.

Figure 4:
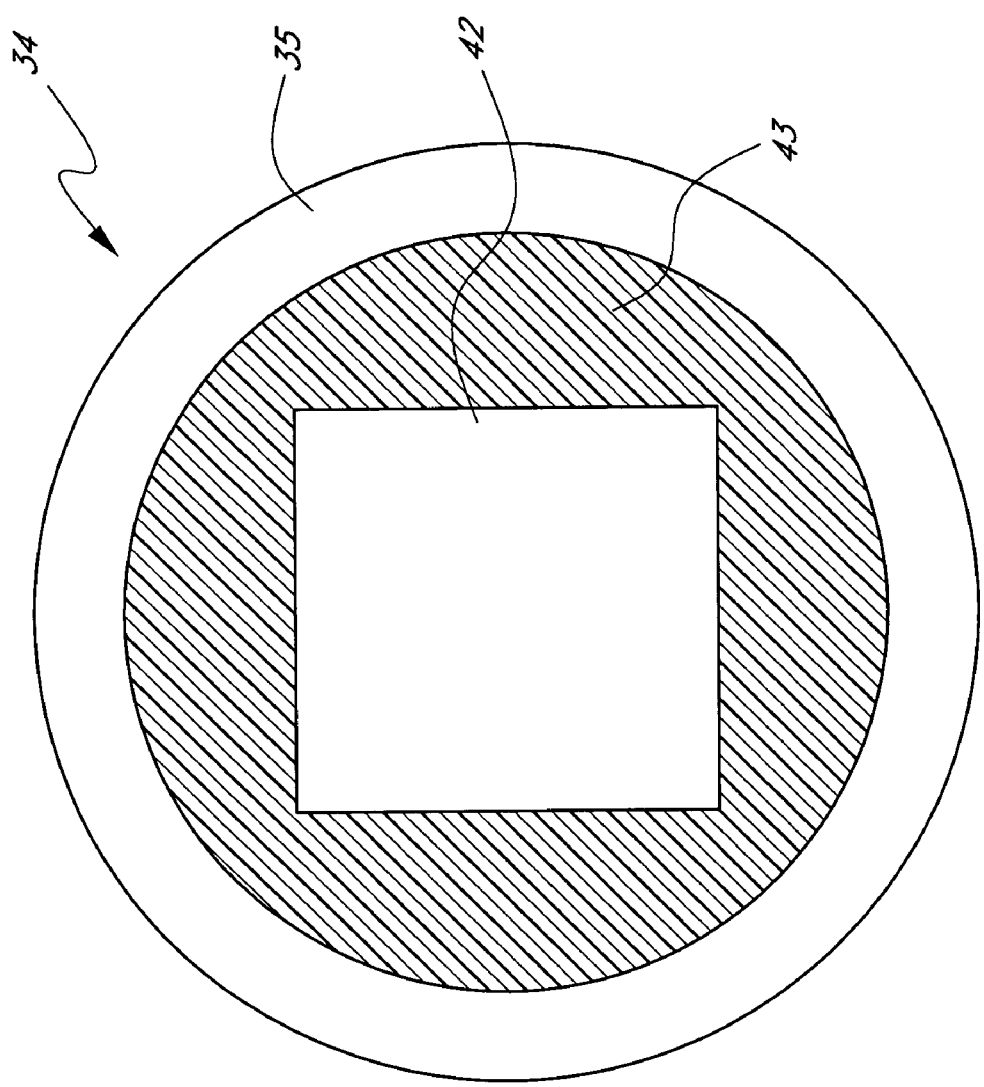
FIG. 4 is a cross-sectional view of the elongate inner core of FIG. 3 taken along line 4—4.

As shown in the cross-section illustrated in FIG. 4, which is taken along lines 4—4 in FIG. 3, the inner core 34 preferably has a cylindrical shape, with an outer diameter that permits the inner core 34 to be inserted into the central lumen 51 of the tubular body 12 via the proximal access port 31. Suitable outer diameters of the inner core 34 include, but are not limited to, about 0.010 inches to about 0.100 inches. In another embodiment, the outer diameter of the inner core 34 is between about 0.020 inches and about 0.080 inches. In yet another embodiment, the inner core 34 has an outer diameter of about 0.035 inches.

Still referring to FIG. 4, the inner core 34 preferably comprises a cylindrical outer body 35 that houses the ultrasound assembly 42. The ultrasound assembly 42 comprises wiring and ultrasound radiating members, described in greater detail in FIGS. 5 through 7D, such that the ultrasound assembly 42 is capable of radiating ultrasonic energy from the energy delivery section 41 of the inner core 34. The ultrasound assembly 42 is electrically connected to the backend hub 33, where the inner core 34 can be connected to control circuitry 100 via cable 45 (illustrated in FIG. 1). Preferably, an electrically insulating potting material 43 fills the inner core 34, surrounding the ultrasound assembly 42, thus preventing movement of the ultrasound assembly 42 with respect to the outer body 35. In one embodiment, the thickness of the outer body 35 is between about 0.0002 inches and 0.010 inches. In another embodiment, the thickness of the outer body 35 is between about 0.0002 inches and 0.005 inches. In yet another embodiment, the thickness of the outer body 35 is about 0.0005 inches.

Figure 5:
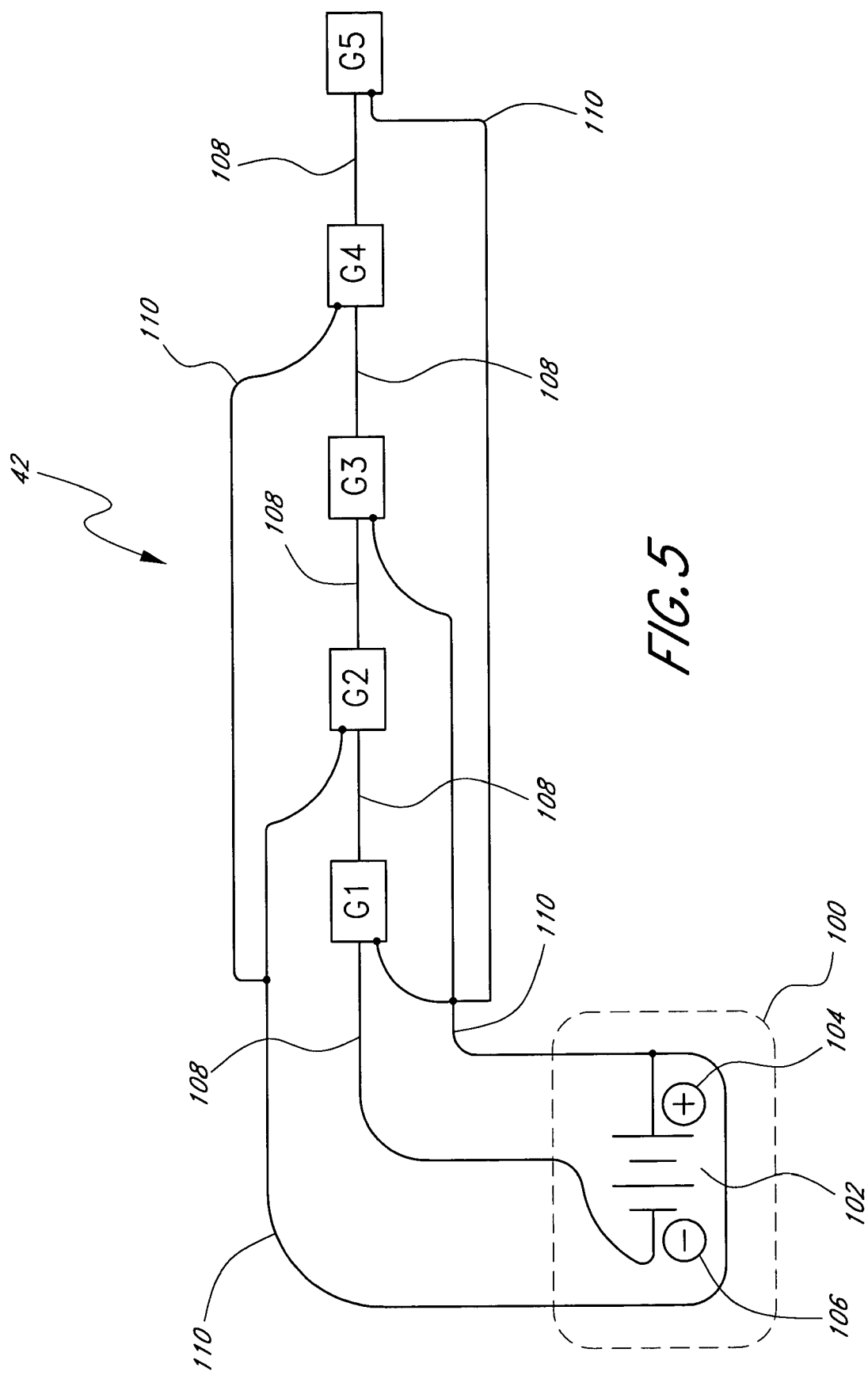
FIG. 5 is a schematic wiring diagram illustrating a preferred technique for electrically connecting five groups of ultrasound radiating members to form an ultrasound assembly.
Figure 6:
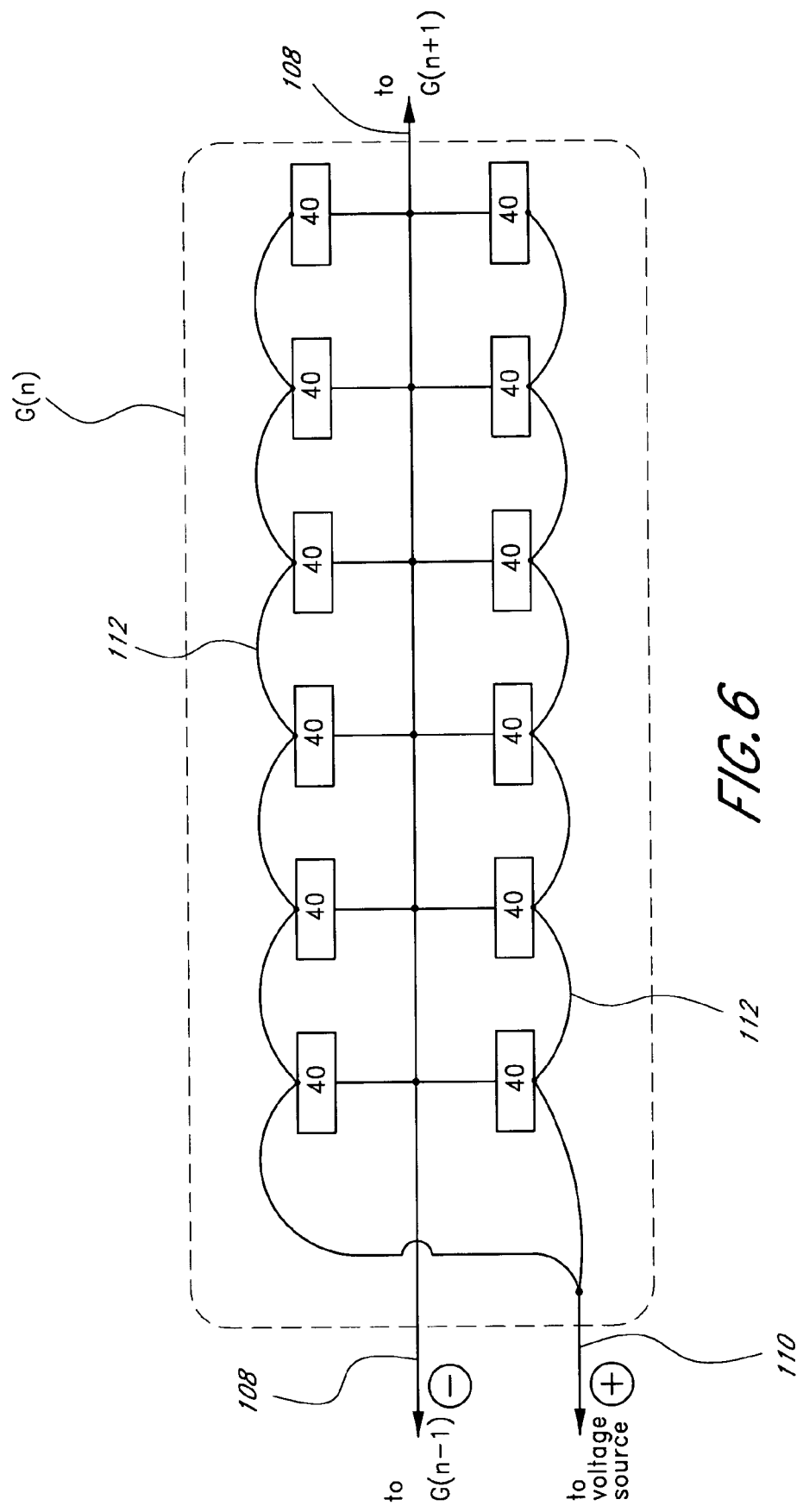
FIG. 6 is a schematic wiring diagram illustrating a preferred technique for electrically connecting one of the groups of FIG. 5.

In a preferred embodiment, the ultrasound assembly 42 comprises a plurality of ultrasound radiating members that are divided into one or more groups. For example, FIGS. 5 and 6 are schematic wiring diagrams illustrating one technique for connecting five groups of ultrasound radiating members 40 to form the ultrasound assembly 42. As illustrated in FIG. 5, the ultrasound assembly 42 comprises five groups G1, G2, G3, G4, G5 of ultrasound radiating members 40 that are electrically connected to each other. The five groups are also electrically connected to the control circuitry 100.

As used herein, the terms "ultrasonic energy", "ultrasound" and "ultrasonic" are broad terms, having their ordinary meanings, and further refer to, without limitation, mechanical energy transferred through longitudinal pressure or compression waves. Ultrasonic energy can be emitted as continuous or pulsed waves, depending on the requirements of a particular application. Additionally, ultrasonic energy can be emitted in waveforms having various shapes, such as sinusoidal waves, triangle waves, square waves, or other wave forms. Ultrasonic energy includes sound waves. In certain embodiments, the ultrasonic energy has a frequency between about 20 kHz and about 20 MHz. For example, in one embodiment, the waves have a frequency between about 500 kHz and about 20 MHz. In another embodiment, the waves have a frequency between about 1 MHz and about 3 MHz. In yet another embodiment, the waves have a frequency of about 2 MHz. The average acoustic power is between about 0.01 watts and 300 watts. In one embodiment, the average acoustic power is about 15 watts.

As used herein, the term "ultrasound radiating member" refers to any apparatus capable of producing ultrasonic energy. For example, in one embodiment, an ultrasound radiating member comprises an ultrasonic transducer, which converts electrical energy into ultrasonic energy. A suitable example of an ultrasonic transducer for generating ultrasonic energy from electrical energy includes, but is not limited to, piezoelectric ceramic oscillators. Piezoelectric ceramics typically comprise a crystalline material, such as quartz, that change shape when an electrical current is applied to the material. This change in shape, made oscillatory by an oscillating driving signal, creates ultrasonic sound waves. In other embodiments, ultrasonic energy can be generated by an ultrasonic transducer that is remote from the ultrasound radiating member, and the ultrasonic energy can be transmitted, via, for example, a wire that is coupled to the ultrasound radiating member.

Still referring to FIG. 5, the control circuitry 100 preferably comprises, among other things, a voltage source 102. The voltage source 102 comprises a positive terminal 104 and a negative terminal 106. The negative terminal 106 is connected to common wire 108, which connects the five groups G1–G5 of ultrasound radiating members 40 in series. The positive terminal 104 is connected to a plurality of lead wires 110, which each connect to one of the five groups G1–G5 of ultrasound radiating members 40. Thus, under this configuration, each of the five groups G1–G5, one of which is illustrated in FIG. 6, is connected to the positive terminal 104 via one of the lead wires 110, and to the negative terminal 106 via the common wire 108.

Referring now to FIG. 6, each group G1–G5 comprises a plurality of ultrasound radiating members 40. Each of the ultrasound radiating members 40 is electrically connected to the common wire 108 and to the lead wire 110 via one of two positive contact wires 112. Thus, when wired as illustrated, a constant voltage difference will be applied to each ultrasound radiating member 40 in the group. Although the group illustrated in FIG. 6 comprises twelve ultrasound radiating members 40, one of ordinary skill in the art will recognize that more or fewer ultrasound radiating members 40 can be included in the group. Likewise, more or fewer than five groups can be included within the ultrasound assembly 42 illustrated in FIG. 5.

Figure 7A:
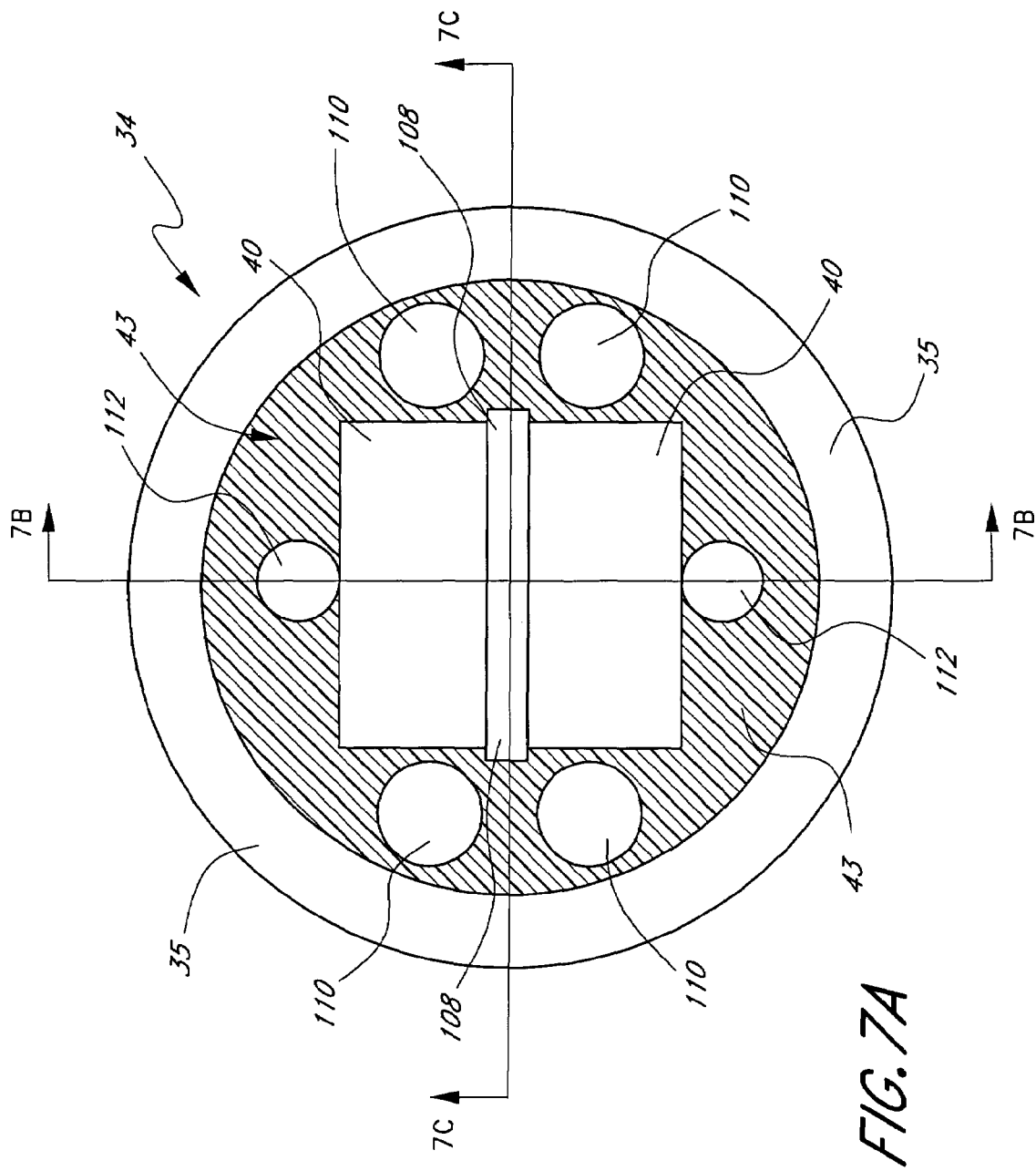
FIG. 7A is a schematic illustration of the ultrasound assembly of FIG. 5 housed within the inner core of FIG. 4.

FIG. 7A illustrates one preferred technique for arranging the components of the ultrasound assembly 42 (as schematically illustrated in FIG. 5) into the inner core 34 (as schematically illustrated in FIG. 4). FIG. 7A is a cross-sectional view of the ultrasound assembly 42 taken within group G1 in FIG. 5, as indicated by the presence of four lead wires 110. For example, if a cross-sectional view of the ultrasound assembly 42 was taken within group G4 in FIG. 5, only one lead wire 110 would be present (that is, the one lead wire connecting group G5).

Referring still to FIG. 7A, the common wire 108 comprises an elongate, flat piece of electrically conductive material in electrical contact with a pair of ultrasound radiating members 40. Each of the ultrasound radiating members 40 is also in electrical contact with a positive contact wire 112. Because the common wire 108 is connected to the negative terminal 106, and the positive contact wire 112 is connected to the positive terminal 104, a voltage difference can be created across each ultrasound radiating member 40. Lead wires 110 are preferably separated from the other components of the ultrasound assembly 42, thus preventing interference with the operation of the ultrasound radiating members 40 as described above. For example, in one preferred embodiment, the inner core 34 is filled with an insulating potting material 43, thus deterring unwanted electrical contact between the various components of the ultrasound assembly 42.

FIGS. 7B and 7C illustrate cross sectional views of the inner core 34 of FIG. 7A taken along lines 7B—7B and 7C—7C, respectively. As illustrated in FIG. 7B, the ultrasound radiating members 40 are mounted in pairs along the common wire 108. The ultrasound radiating members 40 are connected by positive contact wires 112, such that substantially the same voltage is applied to each ultrasound radiating member 40. As illustrated in FIG. 7C, the common wire 108 preferably comprises wide regions 108W upon which the ultrasound radiating members 40 can be mounted, thus reducing the likelihood that the paired ultrasound radiating members 40 will short together. In certain embodiments, outside the wide regions 108W, the common wire 108 may have a more conventional, rounded wire shape.

Figure 7D:
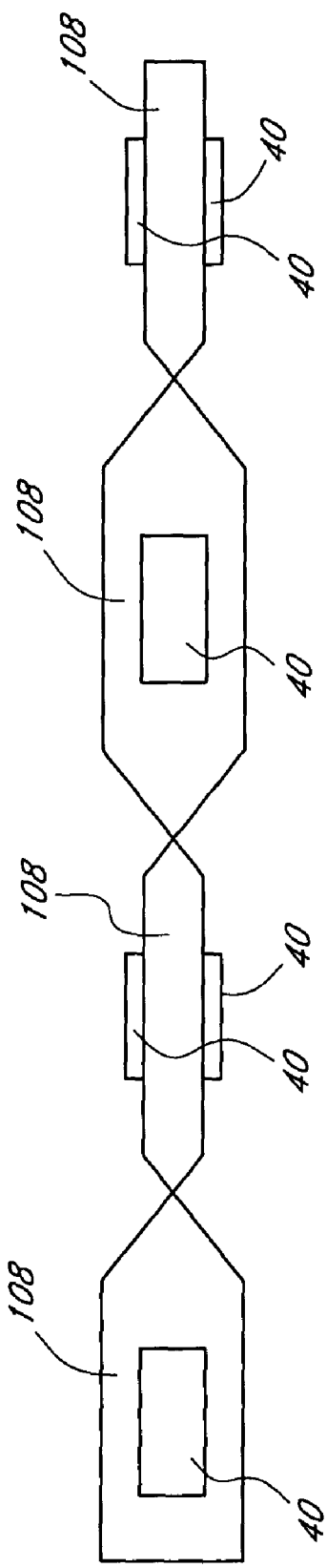
FIG. 7D is a side view of an ultrasound assembly center wire twisted into a helical configuration.

In a modified embodiment, such as illustrated in FIG. 7D, the common wire 108 is twisted to form a helical shape before being fixed within the inner core 34. In such embodiments, the ultrasound radiating members 40 are oriented in a plurality of radial directions, thus enhancing the radial uniformity of the resulting ultrasonic energy field.

One of ordinary skill in the art will recognize that the wiring arrangement described above can be modified to allow each group G1, G2, G3, G4, G5 to be independently powered. Specifically, by providing a separate power source within the control system 100 for each group, each group can be individually turned on or off, or can be driven with an individualized power. This provides the advantage of allowing the delivery of ultrasonic energy to be "turned off" in regions of the treatment site where treatment is complete, thus preventing deleterious or unnecessary ultrasonic energy to be applied to the patient.

The embodiments described above, and illustrated in FIGS. 5 through 7, illustrate a plurality of ultrasound radiating members grouped spatially. That is, in such embodiments, all of the ultrasound radiating members within a certain group are positioned adjacent to each other, such that when a single group is activated, ultrasonic energy is delivered at a specific length of the ultrasound assembly. However, in modified embodiments, the ultrasound radiating members of a certain group may be spaced apart from each other, such that the ultrasound radiating members within a certain group are not positioned adjacent to each other. In such embodiments, when a single group is activated, ultrasonic energy can be delivered from a larger, spaced apart portion of the energy delivery section. Such modified embodiments may be advantageous in applications wherein it is desired to deliver a less focussed, more diffuse ultrasonic energy field to the treatment site.

In a preferred embodiment, the ultrasound radiating members 40 comprise rectangular lead zirconate titanate ("PZT") ultrasound transducers that have dimensions of about 0.017 inches by about 0.010 inches by about 0.080 inches. In other embodiments, other configurations may be used. For example, disc-shaped ultrasound radiating members 40 can be used in other embodiments. In a preferred embodiment, the common wire 108 comprises copper, and is about 0.005 inches thick, although other electrically conductive materials and other dimensions can be used in other embodiments. Lead wires 110 are preferably 36-gauge electrical conductors, while positive contact wires 112 are preferably 42-gauge electrical conductors. However, one of ordinary skill in the art will recognize that other wire gauges can be used in other embodiments.

As described above, suitable frequencies for the ultrasound radiating member 40 include, but are not limited to, from about 20 kHz to about 20 MHz. In one embodiment, the frequency is between about 500 kHz and 20 MHz, and in another embodiment the frequency is between about 1 MHz and 3 MHz. In yet another embodiment, the ultrasound radiating members 40 are operated with a frequency of about 2 MHz.

Figure 8:
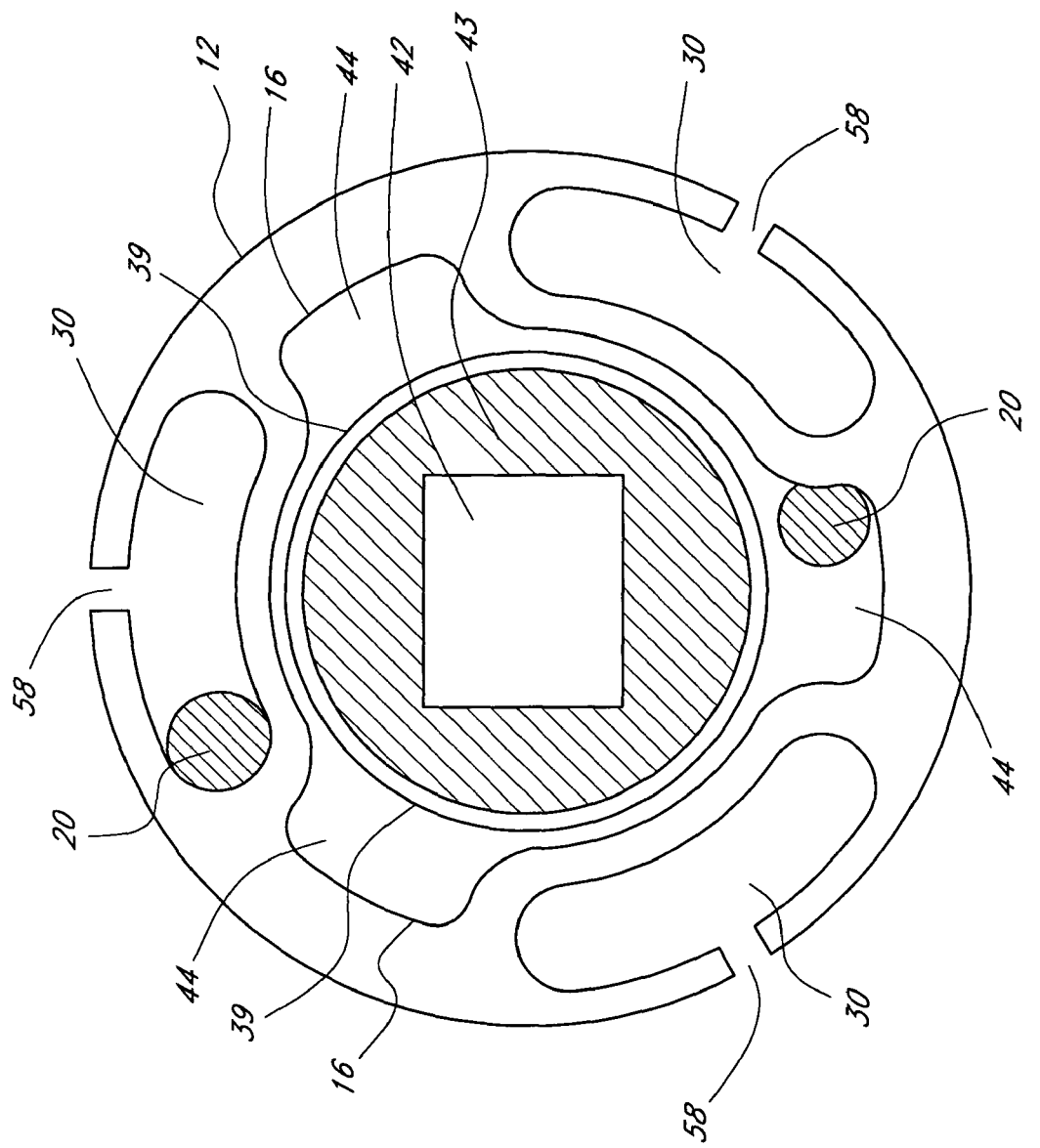
FIG. 8 illustrates the energy delivery section of the inner core of FIG. 4 positioned within the energy delivery section of the tubular body of FIG. 2.

FIG. 8 illustrates the inner core 34 positioned within the tubular body 12. Details of the ultrasound assembly 42, provided in FIG. 7A, are omitted for clarity. As described above, the inner core 34 can be slid within the central lumen 51 of the tubular body 12, thereby allowing the inner core energy delivery section 41 to be positioned within the tubular body energy delivery section 18. For example, in a preferred embodiment, the materials comprising the inner core energy delivery section 41, the tubular body energy delivery section 18, and the potting material 43 all comprise materials having a similar acoustic impedance, thereby minimizing ultrasonic energy losses across material interfaces.

FIG. 8 further illustrates placement of fluid delivery ports 58 within the tubular body energy delivery section 18. As illustrated, holes or slits are formed from the fluid delivery lumen 30 through the tubular body 12, thereby permitting fluid flow from the fluid delivery lumen 30 to the treatment site. Thus, a source of therapeutic compound coupled to the inlet port 32 provides a hydraulic pressure which drives the therapeutic compound through the fluid delivery lumens 30 and out the fluid delivery ports 58.

By evenly spacing the fluid delivery lumens 30 around the circumference of the tubular body 12, as illustrated in FIG. 8, a substantially even flow of therapeutic compound around the circumference of the tubular body 12 can be achieved. In addition, the size, location and geometry of the fluid delivery ports 58 can be selected to provide uniform fluid flow from the fluid delivery lumen 30 to the treatment site. For example, in one embodiment, fluid delivery ports 58 closer to the proximal region of the energy delivery section 18 have smaller diameters than fluid delivery ports 58 closer to the distal region of the energy delivery section 18, thereby allowing uniform delivery of fluid across the entire energy delivery section 18.

For example, in one embodiment in which the fluid delivery ports 58 have similar sizes along the length of the tubular body 12, the fluid delivery ports 58 have a diameter between about 0.0005 inches to about 0.0050 inches. In another embodiment in which the size of the fluid delivery ports 58 changes along the length of the tubular body 12, the fluid delivery ports 58 have a diameter between about 0.001 inches to about 0.005 inches in the proximal region of the energy delivery section 18, and between about 0.005 inches to 0.0020 inches in the distal region of the energy delivery section 18. The increase in size between adjacent fluid delivery ports 58 depends on the material comprising the tubular body 12, and on the size of the fluid delivery lumen 30. The fluid delivery ports 58 can be created in the tubular body 12 by punching, drilling, burning or ablating (such as with a laser), or by any other suitable method. Therapeutic compound flow along the length of the tubular body 12 can also be increased by increasing the density of the fluid delivery ports 58 toward the distal region 15 of the tubular body 12.

It should be appreciated that it may be desirable to provide non-uniform fluid flow from the fluid delivery ports 58 to the treatment site. In such embodiment, the size, location and geometry of the fluid delivery ports 58 can be selected to provide such non-uniform fluid flow.

Referring still to FIG. 8, placement of the inner core 34 within the tubular body 12 further defines cooling fluid lumens 44. Cooling fluid lumens 44 are formed between an outer surface 39 of the inner core 34 and an inner surface 16 of the tubular body 12. In certain embodiments, a cooling fluid is introduced through the proximal access port 31 such that cooling fluid flow is produced through cooling fluid lumens 44 and out distal exit port 29 (see FIG. 1). The cooling fluid lumens 44 are preferably evenly spaced around the circumference of the tubular body 12 (that is, at approximately 120° increments for a three-lumen configuration), thereby providing uniform cooling fluid flow over the inner core 34. Such a configuration is desired to remove unwanted thermal energy at the treatment site. As will be explained below, the flow rate of the cooling fluid and the power to the ultrasound assembly 42 can be adjusted to maintain the temperature of the inner core energy delivery section 41 within a desired range.

In a preferred embodiment, the inner core 34 can be rotated or moved within the tubular body 12. Specifically, movement of the inner core 34 can be accomplished by maneuvering the proximal hub 37 while holding the backend hub 33 stationary. The inner core outer body 35 is at least partially constructed from a material that provides enough structural support to permit movement of the inner core 34 within the tubular body 12 without kinking of the tubular body 12. Additionally, the inner core outer body 35 preferably comprises a material having the ability to transmit torque. Suitable materials for the inner core outer body 35 include, but are not limited to, polyimides, polyesters, polyurethanes, thermoplastic elastomers and braided polyimides.

In a preferred embodiment, the fluid delivery lumens 30 and the cooling fluid lumens 44 are open at the distal end of the tubular body 12, thereby allowing the therapeutic compound and the cooling fluid to pass into the patient's vasculature at the distal exit port. Or, if desired, the fluid delivery lumens 30 can be selectively occluded at the distal end of the tubular body 12, thereby providing additional hydraulic pressure to drive the therapeutic compound out of the fluid delivery ports 58. In either configuration, the inner core 34 can prevented from passing through the distal exit port by configuring the inner core 34 to have a length that is less than the length of the tubular body 12. In other embodiments, a protrusion is formed on the inner surface 16 of the tubular body 12 in the distal region 15, thereby preventing the inner core 34 from passing through the distal exit port 29.

In still other embodiments, the catheter 10 further comprises an occlusion device (not shown) positioned at the distal exit port 29. The occlusion device preferably has a reduced inner diameter that can accommodate a guidewire, but that is less than the outer diameter of the central lumen 51. Thus, the inner core 34 is prevented from extending through the occlusion device and out the distal exit port 29. For example, suitable inner diameters for the occlusion device include, but are not limited to, about 0.005 inches to about 0.050 inches. In other embodiments, the occlusion device has a closed end, thus preventing cooling fluid from leaving the catheter 10, and instead recirculating to the proximal region 14 of the tubular body 12. These and other cooling fluid flow configurations permit the power provided to the ultrasound assembly 42 to be increased in proportion to the cooling fluid flow rate. Additionally, certain cooling fluid flow configurations can reduce exposure of the patient's body to cooling fluids.

In certain embodiments, as illustrated in FIG. 8, the tubular body 12 further comprises one or more temperature sensors 20, which are preferably located within the energy delivery section 18. In such embodiments, the proximal region 14 of the tubular body 12 includes a temperature sensor lead wire (not shown) which can be incorporated into cable 45 (illustrated in FIG. 1). Suitable temperature sensors include, but are not limited to, temperature sensing diodes, thermistors, thermocouples, resistance temperature detectors ("RTDs") and fiber optic temperature sensors which use thermalchromic liquid crystals. Suitable temperature sensor 20 geometries include, but are not limited to, a point, a patch or a stripe. The temperature sensors 20 can be positioned within one or more of the fluid delivery lumens 30, and/or within one or more of the cooling fluid lumens 44.

Figure 9:
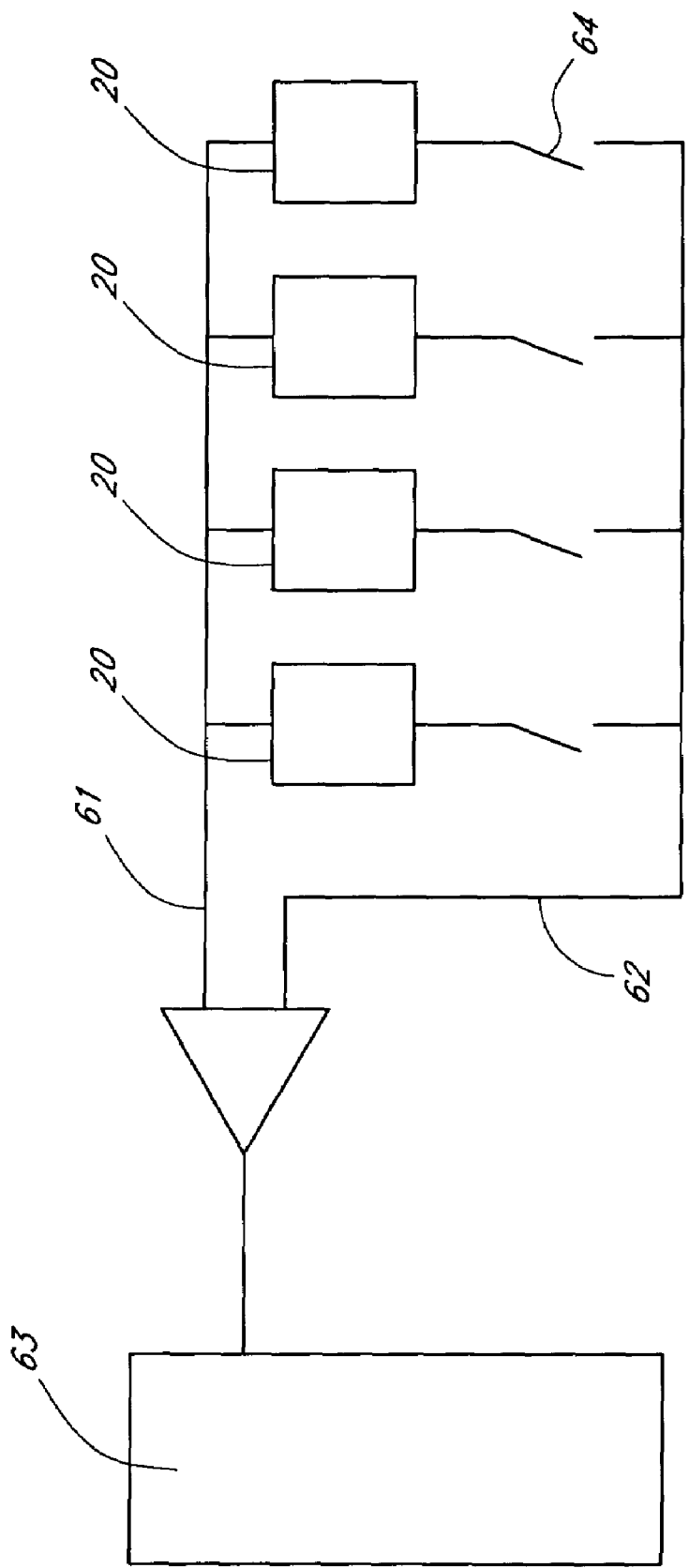
FIG. 9 illustrates a wiring diagram for connecting a plurality of temperature sensors with a common wire.

FIG. 9 illustrates one embodiment for electrically connecting the temperature sensors 20. In such embodiments, each temperature sensor 20 is coupled to a common wire 61 and is associated with an individual return wire 62. Accordingly, n+1 wires can be used to independently sense the temperature at n distinct temperature sensors 20. The temperature at a particular temperature sensor 20 can be determined by closing a switch 64 to complete a circuit between that thermocouple's individual return wire 62 and the common wire 61. In embodiments wherein the temperature sensors 20 comprise thermocouples, the temperature can be calculated from the voltage in the circuit using, for example, a sensing circuit 63, which can be located within the external control circuitry 100.

In other embodiments, each temperature sensor 20 is independently wired. In such embodiments, 2n wires pass through the tubular body 12 to independently sense the temperature at n independent temperature sensors 20. In still other embodiments, the flexibility of the tubular body 12 can be improved by using fiber optic based temperature sensors 20. In such embodiments, flexibility can be improved because only n fiber optic members are used to sense the temperature at n independent temperature sensors 20.

Figure 10:
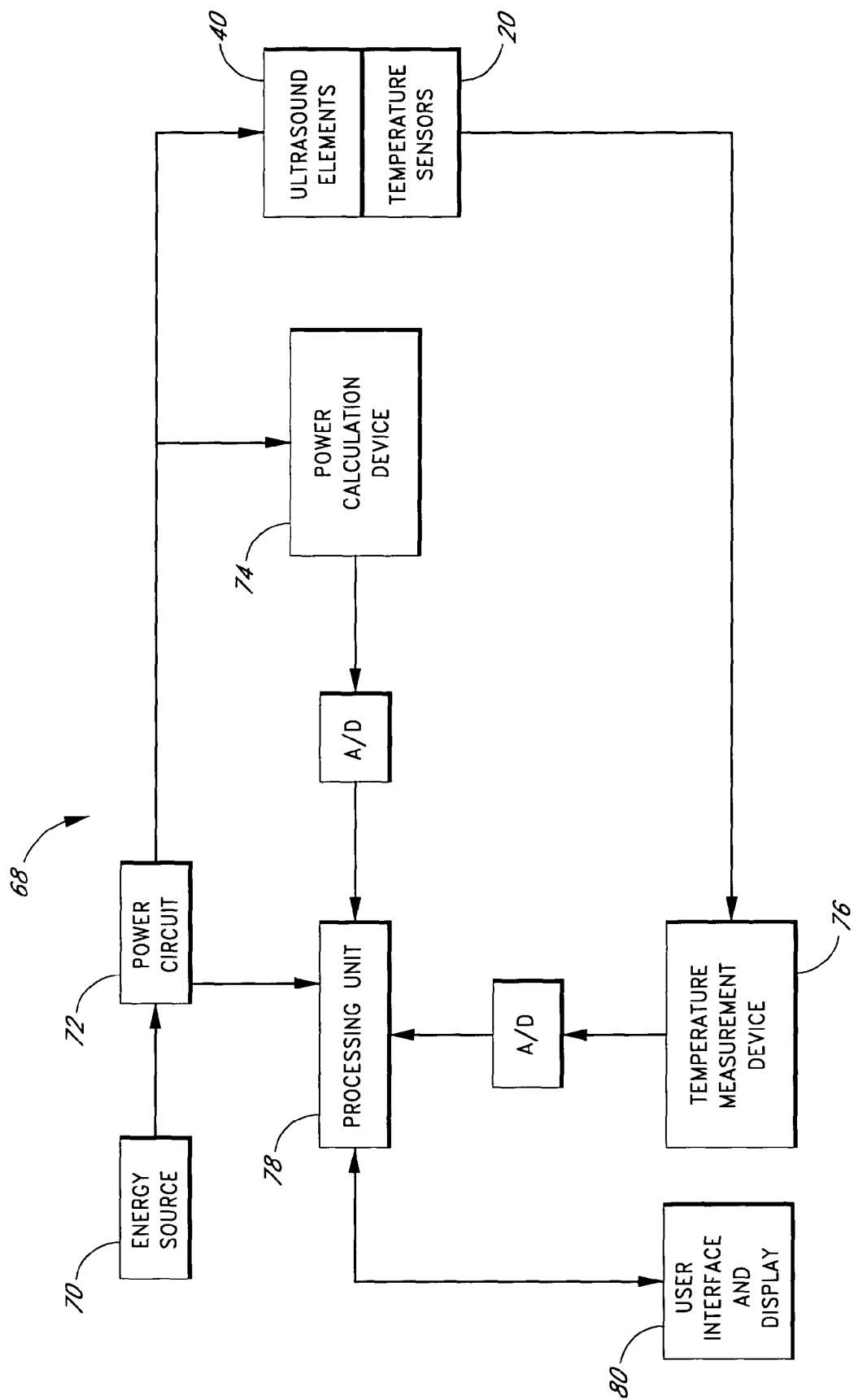
FIG. 10 is a block diagram of a feedback control system for use with an ultrasonic catheter.

FIG. 10 illustrates one embodiment of a feedback control system 68 that can be used with the catheter 10. The feedback control system 68 can be integrated into the control system that is connected to the inner core 34 via cable 45 (as illustrated in FIG. 1). The feedback control system 68 allows the temperature at each temperature sensor 20 to be monitored and allows the output power of the energy source 70 to be adjusted accordingly. A physician can, if desired, override the closed or open loop system.

The feedback control system 68 preferably comprises an energy source 70, power circuits 72 and a power calculation device 74 that is coupled to the ultrasound radiating members 40. A temperature measurement device 76 is coupled to the temperature sensors 20 in the tubular body 12. A processing unit 78 is coupled to the power calculation device 74, the power circuits 72 and a user interface and display 80.

In operation, the temperature at each temperature sensor 20 is determined by the temperature measurement device 76. The processing unit 78 receives each determined temperature from the temperature measurement device 76. The determined temperature can then be displayed to the user at the user interface and display 80.

The processing unit 78 comprises logic for generating a temperature control signal. The temperature control signal is proportional to the difference between the measured temperature and a desired temperature. The desired temperature can be determined by the user (set at the user interface and display 80) or can be preset within the processing unit 78.

The temperature control signal is received by the power circuits 72. The power circuits 72 are preferably configured to adjust the power level, voltage, phase and/or current of the electrical energy supplied to the ultrasound radiating members 40 from the energy source 70. For example, when the temperature control signal is above a particular level, the power supplied to a particular group of ultrasound radiating members 40 is preferably reduced in response to that temperature control signal. Similarly, when the temperature control signal is below a particular level, the power supplied to a particular group of ultrasound radiating members 40 is preferably increased in response to that temperature control signal. After each power adjustment, the processing unit 78 preferably monitors the temperature sensors 20 and produces another temperature control signal which is received by the power circuits 72.

The processing unit 78 preferably further comprises safety control logic. The safety control logic detects when the temperature at a temperature sensor 20 has exceeded a safety threshold. The processing unit 78 can then provide a temperature control signal which causes the power circuits 72 to stop the delivery of energy from the energy source 70 to that particular group of ultrasound radiating members 40.

Because, in certain embodiments, the ultrasound radiating members 40 are mobile relative to the temperature sensors 20, it can be unclear which group of ultrasound radiating members 40 should have a power, voltage, phase and/or current level adjustment. Consequently, each group of ultrasound radiating member 40 can be identically adjusted in certain embodiments. In a modified embodiment, the power, voltage, phase, and/or current supplied to each group of ultrasound radiating members 40 is adjusted in response to the temperature sensor 20 which indicates the highest temperature. Making voltage, phase and/or current adjustments in response to the temperature sensed by the temperature sensor 20 indicating the highest temperature can reduce overheating of the treatment site.

The processing unit 78 also receives a power signal from a power calculation device 74. The power signal can be used to determine the power being received by each group of ultrasound radiating members 40. The determined power can then be displayed to the user on the user interface and display 80.

As described above, the feedback control system 68 can be configured to maintain tissue adjacent to the energy delivery section 18 below a desired temperature. For example, it is generally desirable to prevent tissue at a treatment site from increasing more than 6° C. As described above, the ultrasound radiating members 40 can be electrically connected such that each group of ultrasound radiating members 40 generates an independent output. In certain embodiments, the output from the power circuit maintains a selected energy for each group of ultrasound radiating members 40 for a selected length of time.

The processing unit 78 can comprise a digital or analog controller, such as for example a computer with software. When the processing unit 78 is a computer it can include a central processing unit ("CPU") coupled through a system bus. As is well known in the art, the user interface and display 80 can comprise a mouse, a keyboard, a disk drive, a display monitor, a nonvolatile memory system, or any another. Also preferably coupled to the bus is a program memory and a data memory.

In lieu of the series of power adjustments described above, a profile of the power to be delivered to each group of ultrasound radiating members 40 can be incorporated into the processing unit 78, such that a preset amount of ultrasonic energy to be delivered is pre-profiled. In such embodiments, the power delivered to each group of ultrasound radiating members 40 can then be adjusted according to the preset profiles.

The ultrasound radiating members 40 are preferably operated in a pulsed mode. For example, in one embodiment, the time average power supplied to the ultrasound radiating members 40 is preferably between about 0.1 watts and 2 watts and more preferably between about 0.5 watts and 1.5 watts. In certain preferred embodiments, the time average power is approximately 0.6 watts or 1.2 watts. The duty cycle is preferably between about 1% and 50% and more preferably between about 5% and 25%. In certain preferred embodiments, the duty ratio is approximately 7.5% or 15%. The pulse averaged power is preferably between about 0.1 watts and 20 watts and more preferably between approximately 5 watts and 20 watts. In certain preferred embodiments, the pulse averaged power is approximately 8 watts and 16 watts. The amplitude during each pulse can be constant or varied.

In one embodiment, the pulse repetition rate is preferably between about 5 Hz and 150 Hz and more preferably between about 10 Hz and 50 Hz. In certain preferred embodiments, the pulse repetition rate is approximately 30 Hz. The pulse duration is preferably between about 1 millisecond and 50 milliseconds and more preferably between about 1 millisecond and 25 milliseconds. In certain preferred embodiments, the pulse duration is approximately 2.5 milliseconds or 5 milliseconds.

In one particular embodiment, the ultrasound radiating members 40 are operated at an average power of approximately 0.6 watts, a duty cycle of approximately 7.5%, a pulse repetition rate of 30 Hz, a pulse average electrical power of approximately 8 watts and a pulse duration of approximately 2.5 milliseconds.

The ultrasound radiating members 40 used with the electrical parameters described herein preferably has an acoustic efficiency greater than 50% and more preferably greater than 75%. The ultrasound radiating members 40 can be formed a variety of shapes, such as, cylindrical (solid or hollow), flat, bar, triangular, and the like. The length of the ultrasound radiating members 40 is preferably between about 0.1 cm and about 0.5 cm. The thickness or diameter of the ultrasound radiating members 40 is preferably between about 0.02 cm and about 0.2 cm.

Figure 11C:
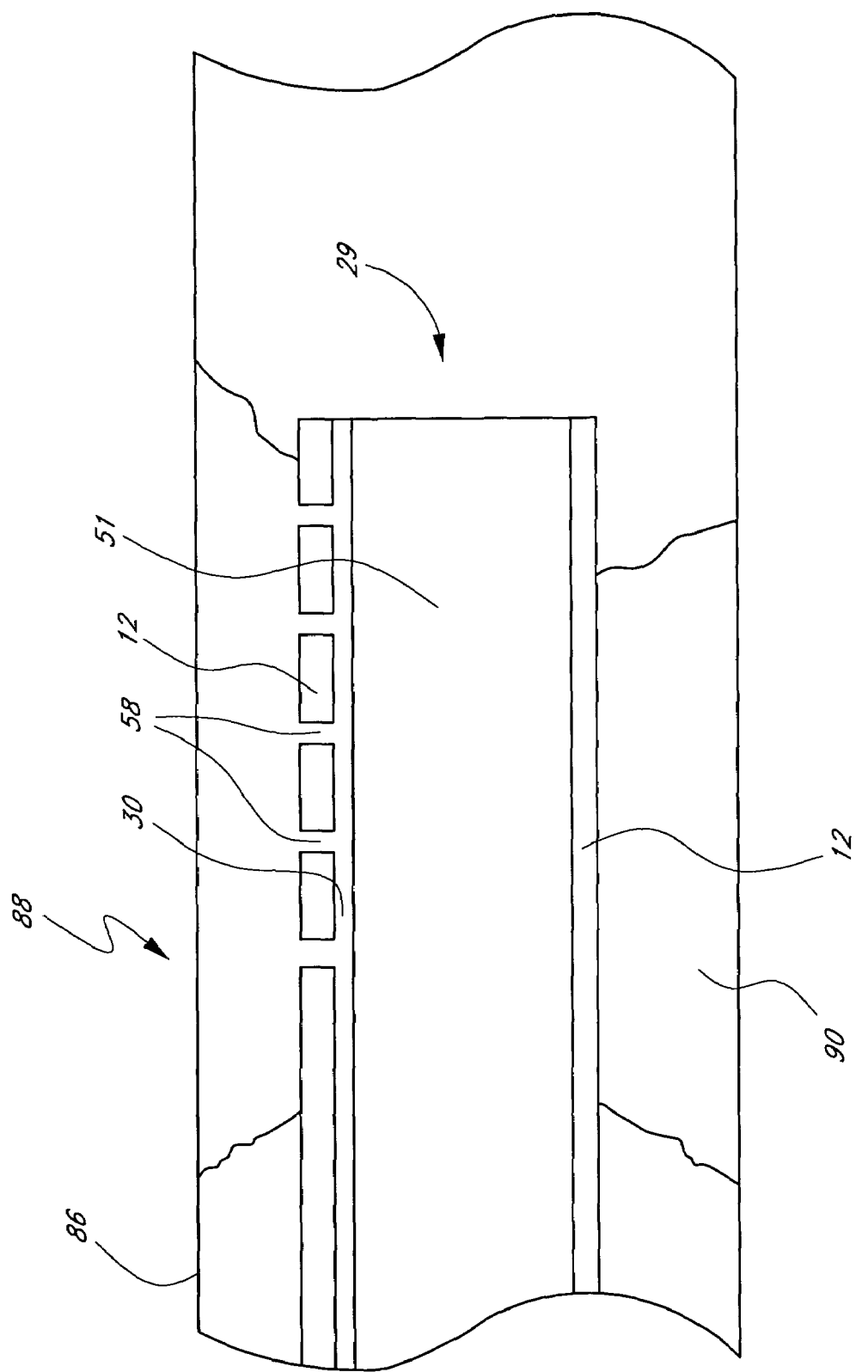
FIG. 11C is a cross-sectional view of the distal end of the ultrasonic catheter of FIG. 11B positioned at the treatment site before a treatment.

FIGS. 11A through 11D illustrate a method for using the ultrasonic catheter 10. As illustrated in FIG. 11A, a guidewire 84 similar to a guidewire used in typical angioplasty procedures is directed through a patient's vessels 86 to a treatment site 88 which includes a clot 90. The guidewire 84 is directed through the clot 90. Suitable vessels 86 include, but are not limited to, the large periphery and the small cerebral blood vessels of the body. Additionally, as mentioned above, the ultrasonic catheter 10 also has utility in various imaging applications or in applications for treating and/or diagnosing other diseases in other body parts.

As illustrated in FIG. 1B, the tubular body 12 is slid over and is advanced along the guidewire 84 using conventional over-the-guidewire techniques. The tubular body 12 is advanced until the energy delivery section 18 of the tubular body 12 is positioned at the clot 90. In certain embodiments, radiopaque markers (not shown) are positioned along the energy delivery section 18 of the tubular body 12 to aid in the positioning of the tubular body 12 within the treatment site 88.

As illustrated in FIG. 11C, the guidewire 84 is then withdrawn from the tubular body 12 by pulling the guidewire 84 from the proximal region 14 of the catheter 10 while holding the tubular body 12 stationary. This leaves the tubular body 12 positioned at the treatment site 88.

Figure 11D:
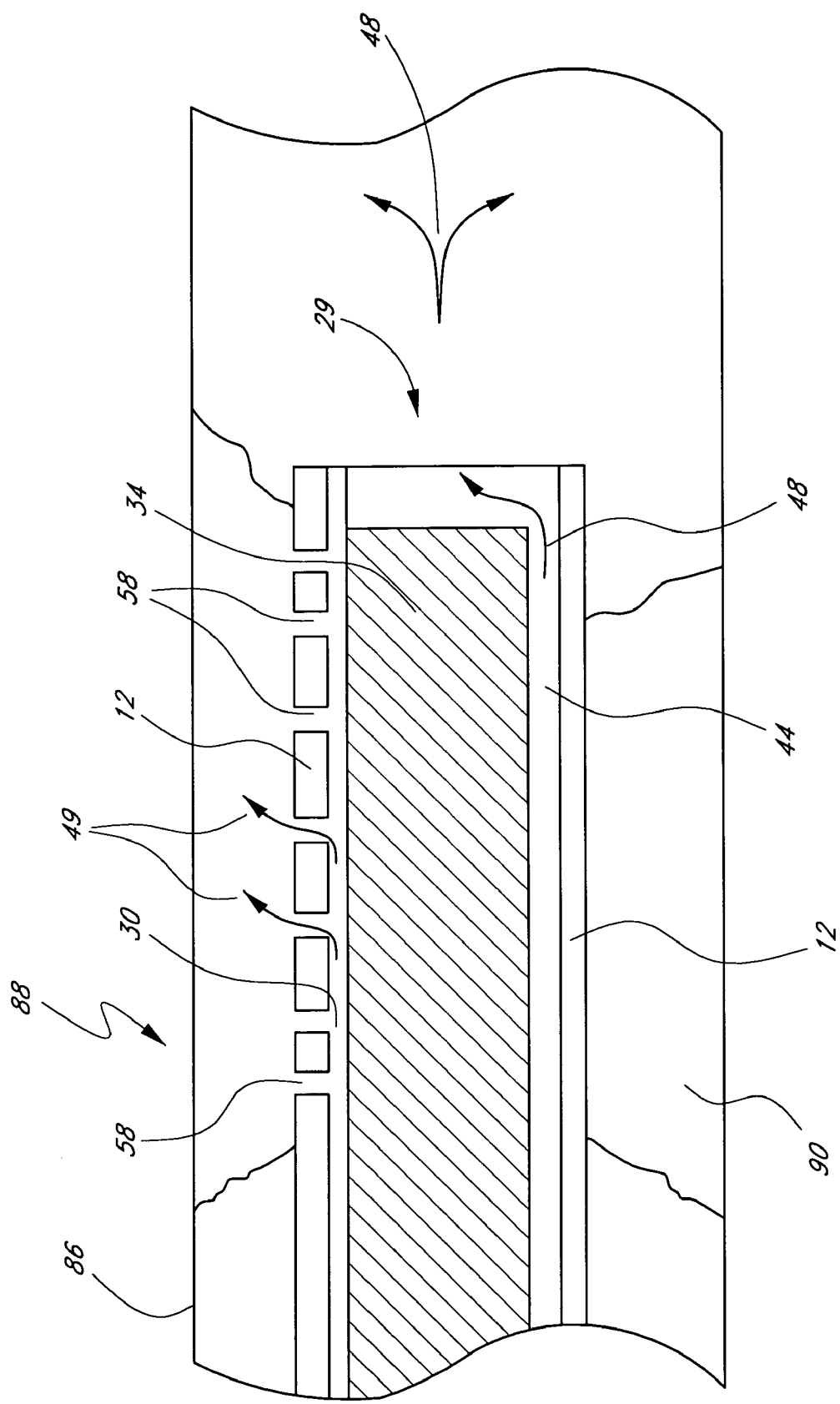
FIG. 11D is a cross-sectional view of the distal end of the ultrasonic catheter of FIG. 11C, wherein an inner core has been inserted into the tubular body to perform a treatment.

As illustrated in FIG. 11D, the inner core 34 is then inserted into the tubular body 12 until the ultrasound assembly is positioned at least partially within the energy delivery section 18 of the tubular body 12. Once the inner core 34 is properly positioned, the ultrasound assembly 42 is activated to deliver ultrasonic energy through the energy delivery section 18 to the clot 90. As described above, in one embodiment, suitable ultrasonic energy is delivered with a frequency between about 20 kHz and about 20 MHz.

In a certain embodiment, the ultrasound assembly 42 comprises sixty ultrasound radiating members 40 spaced over a length between approximately 30 cm and 50 cm. In such embodiments, the catheter 10 can be used to treat an elongate clot 90 without requiring movement of or repositioning of the catheter 10 during the treatment. However, it will be appreciated that in modified embodiments the inner core 34 can be moved or rotated within the tubular body 12 during the treatment. Such movement can be accomplished by maneuvering the proximal hub 37 of the inner core 34 while holding the backend hub 33 stationary.

Referring again to FIG. 11D, arrows 48 indicate that a cooling fluid flows through the cooling fluid lumen 44 and out the distal exit port 29. Likewise, arrows 49 indicate that a therapeutic compound flows through the fluid delivery lumen 30 and out the fluid delivery ports 58 to the treatment site 88.

The cooling fluid can be delivered before, after, during or intermittently with the delivery of ultrasonic energy. Similarly, the therapeutic compound can be delivered before, after, during or intermittently with the delivery of ultrasonic energy. Consequently, the steps illustrated in FIGS. 11A through 11D can be performed in a variety of different orders than as described above. The therapeutic compound and ultrasonic energy are preferably applied until the clot 90 is partially or entirely dissolved. Once the clot 90 has been dissolved to the desired degree, the tubular body 12 and the inner core 34 are withdrawn from the treatment site 88.

Determining Blood Flow Reestablishment

As described above, the various embodiments of the ultrasound catheters disclosed herein can be used with a therapeutic compound to dissolve a clot and reestablish blood flow in a blood vessel. After the clot is sufficiently dissolved and blood flow is reestablished, it is generally undesirable to continue to administer the therapeutic compound and/or ultrasonic energy. For example, the therapeutic compound can have adverse side effects such that it is generally undesirable to continue to administer the therapeutic compound after blood flow has been reestablished. In addition, generating ultrasonic energy tends to create heat, which can damage the blood vessel. It is therefore generally undesirable to continue operating the ultrasound radiating members after the clot has been sufficiently dissolved. Moreover, after blood flow has been reestablished, the treatment of the patient may need to move to another stage. Thus, it is desired to develop a method and apparatus that can determine when the clot has been sufficiently dissolved and/or when blood flow has been sufficiently reestablished such that the treatment can be stopped and/or adjusted.

It is also desirable to measure or monitor the degree to which a clot has been dissolved and/or correspondingly the degree to which blood flow has been reestablished. Such information could be used to determine the effectiveness of the treatment. For example, if the blood flow is being reestablished too slowly, certain treatment parameters (for example, flow of therapeutic compound, ultrasound frequency, ultrasound power, ultrasound pulsing parameters, position of the ultrasound radiating members, and so forth) can be adjusted or modified to increase the effectiveness of the treatment. In other instances, after blood flow is reestablished the treatment may be halted to prevent unnecessary delivery of drug and ultrasound energy. In yet another instance, information on treatment effectiveness can be used to determine if an ultrasound radiating member has malfunctioned. Thus, it is also desired to develop a method and/or an apparatus for determining the degree to which a clot has been dissolved and/or the degree to which blood flow has been reestablished.

It will be appreciated that such methods and apparatuses for determining when blood flow has been reestablished and/or the degree to which blood flow has been reestablished also have utility outside the context of ultrasonic catheters. For example, such information can be used in conjunction with other technologies and methodologies that are used to clear an obstruction in a blood vessel (for example, angioplasty, laser treatments, therapeutic compounds used without ultrasonic energy or with other sources of energy, and so forth). Such techniques can also be used with catheters configured to clot dissolution in both the large and small vasculature.

The methods and apparatuses for determining when blood flow has been reestablished and/or the degree to which blood flow has been reestablished, as disclosed herein, can be used with a feedback control system. For example, one compatible feedback control system is described above with reference to FIG. 10. In general, the feedback control system can be a closed or open loop system that is configured to adjust the treatment parameters in response to the data received from the apparatus. The physician can, if desired, override the closed or open loop system. In other arrangements, the data can be displayed to the physician or a technician such that the physician or technician can adjust treatment parameters and/or make decisions as to the treatment of the patient.

In one embodiment, one or more temperature sensors positioned on or within the catheter can be used to detect and/or measure the reestablishment of blood flow at a clot dissolution treatment site. The temperature sensor can be used to measure and analyze the temperature of the cooling fluid, the therapeutic compound and/or the blood surrounding the catheter. For example, in one arrangement, temperature sensors can be mounted on the outside of the catheter, on the ultrasound radiating members in the inner core, or in any of the fluid lumens to detect differential temperatures of the blood, cooling fluid, or therapeutic compound along the catheter length as a function of time. See, for example, the positioning of the temperature sensors 20 illustrated in FIG. 8.

Figure 12:
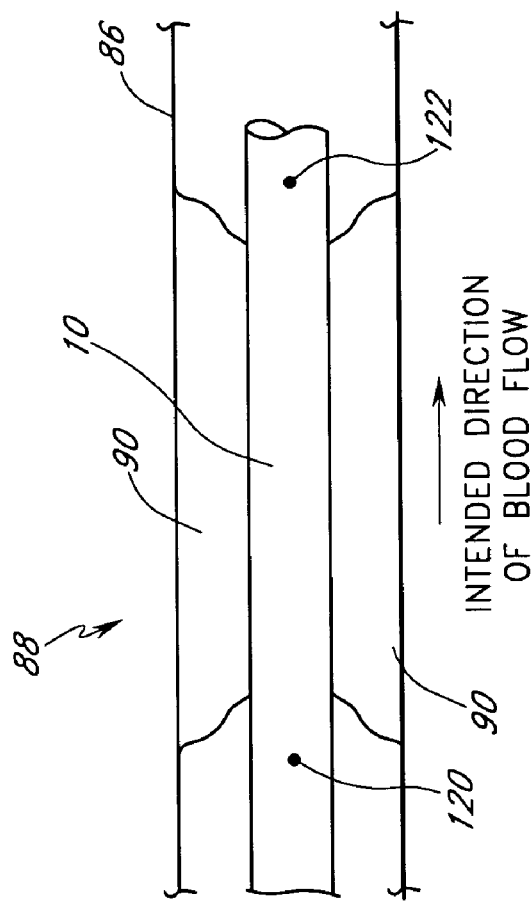
FIG. 12 is a schematic diagram illustrating one arrangement for using thermal measurements for detecting reestablishment of blood flow.

A preferred embodiment for using thermal measurements to detect and/or measure the reestablishment of blood flow during a clot dissolution treatment is illustrated schematically in FIG. 12. A catheter 10 is positioned through a clot 90 at a treatment site 88 in a patient's vasculature 86. The catheter 10 includes at least an upstream thermal source 120 and a downstream thermal detector 122.

The thermal source 120 and thermal detector 122 can be positioned on, within, or integral with the catheter 10. The thermal source 120 comprises any source of thermal energy, such as a resistance heater. For example, in one embodiment, one or more of the ultrasound radiating members comprising the ultrasound assembly can function as a source of thermal energy. However, it will be recognized that the techniques disclosed herein can also be used with a catheter that does not comprise ultrasound radiating members. The thermal detector 122 comprises any device capable of detecting the presence (or absence) of thermal energy, such as a diode, thermistor, thermocouple, and so forth. In one embodiment, one or more of the ultrasound radiating members can be used as a thermal detector by measuring changes in their electrical characteristics (such as, for example, impedance or resonating frequency).

In such embodiments, the thermal source 120 supplies thermal energy into its surrounding environment. For example, if the thermal source 120 is affixed to the outer surface of the catheter 10, then thermal energy is supplied into the surrounding bloodstream. Likewise, if the thermal source is positioned within the fluid delivery lumens 30 and/or the cooling fluid lumens 44 (illustrated in FIG. 8), then thermal energy is supplied into the fluid contained therein.

Figure 13B:
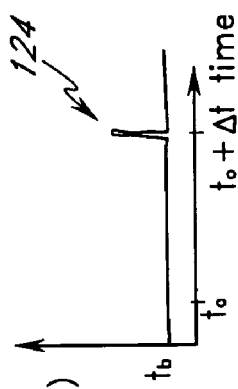
FIG. 13B is an exemplary plot of temperature as a function of time at a thermal detector
Figure 13A:
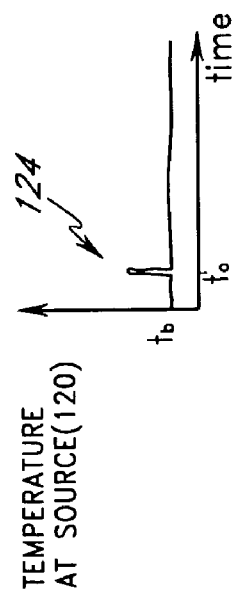
FIG. 13A is an exemplary plot of temperature as a function of time at a thermal source.

FIG. 13A illustrates that when the thermal source 120 supplies thermal energy into the surrounding environment, a "thermal pulse" 124 is created therein. For example, if the thermal source 120 is affixed to the outer surface of the catheter 10 or is affixed within the fluid delivery lumens 30 and/or the cooling fluid lumens 44 (illustrated in FIG. 8), then a thermal pulse 124 is created therein. If the medium into which thermal energy is supplied has a flow rate, then the thermal pulse 124 will propagate with the medium. The thermal pulse 124 can propagate, for example, by mass transfer (that is, due to physical movement of the heated medium) or by thermal conduction (that is, due to thermal energy propagating through a stationary medium). For example, if thermal energy is supplied into a cooling fluid lumen through which a cooling fluid is flowing, then the resultant thermal pulse 124 will likewise flow downstream through the cooling fluid lumen. Similarly, if thermal energy is supplied into the surrounding bloodstream, and if the bloodstream is not completely occluded, then the resultant thermal pulse 124 will flow downstream through the patient's vasculature 86. In other embodiments, the thermal pulse 124 can propagate according to other thermal propagation mechanisms.

As the thermal pulse 124 propagates downstream, the characteristics of the thermal pulse 124 will change. For example, some of the excess thermal energy in the thermal pulse 124 will dissipate into surrounding tissues and/or surrounding catheter structures, thereby reducing the intensity of the thermal pulse 124. Additionally, as the thermal pulse 124 passes through and/or reflects from various materials (such as, for example, clot, blood, tissue, and so forth), the pulse width may increase. When the thermal pulse 124 reaches the thermal detector 122, its characteristics can be measured and analyzed, thereby providing information about blood flow at the treatment site 88.

For example, in certain applications the characteristics (such as, for example, pulse width and intensity) of a thermal pulse supplied from the exterior of the catheter to the surrounding bloodstream will remain substantially unchanged between the thermal source and the thermal detector. This indicates that little thermal energy dissipated into surrounding tissues between the thermal source and the thermal detector, and therefore that the thermal pulse propagated rapidly (that is, high blood flow rate at the treatment site). In other applications, the same characteristics of a thermal pulse supplied from the exterior of the catheter to the surrounding bloodstream will substantially change between the thermal source and the thermal detector. This indicates that a substantial amount of thermal energy dissipated into surrounding tissues between the thermal source and the thermal detector, and therefore that the thermal pulse propagated slowly (that is, low blood flow rate at the treatment site).

In applications where the thermal pulse is supplied from and detected in one of the fluid lumens positioned in the interior of the catheter, reestablishment of blood flow can be evaluated based on the thermal pulse intensity reduction. Specifically, as a clot dissolution treatment progresses, less clot material will be available to absorb energy from the thermal pulse. Thus, in such applications, a high thermal pulse intensity reduction indicates little clot dissolution has occurred, while a low thermal pulse intensity reduction indicates that the clot dissolution treatment has progressed significantly.

Moreover, the amount of time required for the thermal pulse 124 to propagate from the thermal source 120 to the thermal detector 122 provides an indication of the propagation speed of the pulse, thus providing a further indication of blood flow rate at the treatment site 88. Specifically, FIGS. 13A and 13B illustrate that a thermal pulse 124 created at the thermal source 120 at time $t_o$ can be detected at the thermal detector 122 at a later time $t_o + \Delta t$. The time differential $\Delta t$, along with the distance between the thermal source 120 and the thermal detector 122 can provide information about the blood flow rate between those two points, thereby allowing the progression of a clot dissolution treatment to be evaluated.

One of ordinary skill in the art will recognize that the thermal pulse 124 need not be a single spike, as illustrated in FIG. 13, but rather can be a square wave or a sinusoidal signal. In such embodiments, if the thermal signal is delivered into the bloodstream, a thermal signal phase shift between the thermal source and the thermal detector provides a measure of the volumetric flow rate between such points. This provides yet another variable for evaluating the progression of a clot dissolution treatment.

In yet another preferred embodiment, the catheter comprises a temperature sensor without a thermal source. See, for example, the embodiment illustrated in FIG. 8. By monitoring the temperature as a function of time during a clot dissolution treatment, information relating to the efficacy of the treatment can be determined. In particular, as the treatment progresses, blood flow around the catheter will increase, thereby reducing the temperature at the treatment site: the blood flow acts as a supplemental cooling fluid. Thus, a temperature curve for the treatment can be created. Several different types of known curve fitting methods may be used, such as, for example, standard or non-linear curve fitting models, and typical shape function methodology. For more information, see U.S. Pat. No. 5,797,395 and the references identified therein, which are hereby incorporated by reference herein.

The shape of a reference time-temperature curve can be determined under reference conditions. During the clot dissolution treatment, the shape of the time-temperature curve can be compared to the reference time-temperature curve, and significant alternations can trigger the processing unit 78 to trigger an alarm via the user interface and display 80 (see FIG. 10).

It will be recognized that blood flow evaluations can be made based on algorithms other than the thermal pulse delay, thermal dilution, and thermal signal phase shift algorithms disclosed herein. In particular, certain of the concepts disclosed herein can be applied to optical, Doppler, electromagnetic, and other flow evaluation algorithms some of which are described below.

For example, in one modified embodiment, the distal region of the catheter includes an optical sensing system, such as, for example, a fiber optic or pass detector, to determine the degree to which a clot has been dissolved and/or the degree to which blood flow has been reestablished. For example, in one arrangement, the therapeutic compound may contain fluorescent indicators and the sensing system can be used to observe the intrinsic fluorescence of the therapeutic compound or extrinsic fluorescent indicators that are provided in the therapeutic compound. In this manner, the optical sensing system can be used to differentiate between a condition where a therapeutic compound is located proximal to a clotted area (that is, a substantially obstructed vessel) and a condition where predominately blood is located around a previously clotted area (that is, a substantially unobstructed vessel). In another arrangement, a color detector can be used to monitor the fluid color around the clotted area to differentiate between a substantially clot and therapeutic compound condition (that is, a substantially obstructed vessel) and a substantially blood only condition (this is, a substantially open vessel). In yet another arrangement, the color detector can be used to differentiate between the walls of the blood vessel (that is, open vessel) and a clot (that is, obstructed vessel). In still other arrangements, the sensing system can be configured to sense differences outside the visible light range. For example, an infrared detection system can be configured to sense differences between the walls of the blood vessel and a clot.

In such embodiments, the optical sensor can be positioned upstream, downstream and/or within the clot. The optical measurements can be correlated with clinical data so as to quantify the degree to which blood flow has been reestablished.

In another embodiment, the catheter can be configured to use a Doppler frequency shift and/or flight to determine if blood flow has been reestablished. That is, the frequency shift of the ultrasonic energy as it passes through a clotted vessel and/or the time required for the ultrasonic energy to pass through a clotted vessel can be used to determine the degree to which the clot has been dissolved. In one arrangement, this can be accomplished internally using the ultrasound radiating members of the catheter and/or using ultrasonic receiving members positioned in the catheter. In another arrangement, the sensing ultrasonic energy can be generated outside the patient's body and/or received outside the patient's body (for example, via a cuff placed around the treatment site).

In yet another embodiment, blood pressure could be used to determine blood flow reestablishment. In one arrangement, the ultrasound radiating members can be used to detect pressure in the internal fluid column. In other arrangements, individual sensors or lumens can be used.

In another embodiment, a sensor can be configured to monitor the color or temperature of a portion of the patient's body that is affected by the clot. For example, for a clot in the leg, toe color and temperature indicates reestablished blood flow in the leg. As with all the embodiments described herein, such information can be integrated into a control feedback system as described above.

In another embodiment, an accelerometer or motion detector can be configured to sense the vibration in the catheter or in a portion of the patient's body caused by reestablished blood flow.

In another embodiment, one or more electromagnetic flow sensors can be used to sense reestablished blood flow near the clotted area.

In another embodiment, markers (for example, dye, bubbles, cold, heat, and so forth) can be injected into the blood vessel through one or more lumens in the catheter. For example, the marker can be injected at an upstream point. Sensing the passage of such markers past a detector positioned downstream of the upstream injection point indicates blood flow. The rate of passage indicates the degree to which blood flow has been reestablished.

In another embodiment, an external plethysmograph band can be used to determine blood flow. This could be oriented with respect to the catheter radially or in another dimension.

In another embodiment, blood oxygenation can be used to determine the presence of blood flow.

While the foregoing detailed description has described several embodiments of the apparatus and methods of the present invention, it is to be understood that the above description is illustrative only and not limited to the disclosed invention. It will be appreciated that the specific dimensions of the various catheters and inner cores can differ from those described above, and that the methods described can be used within any biological conduit in a patient's body, while remaining within the scope of the present invention. In particular, the methods for evaluating the efficacy of a clot dissolution treatment can be used to evaluate treatments performed with a the peripheral catheter disclosed herein, as wan as with the small vessel catheter disclosed in U.S. patent application Ser. No. 10/309,417, filed Dec. 3, 2002. Thus, the present invention is to be limited only by the claims that follow.

We claim:

1. A method for monitoring clot dissolution in a patient's vasculature, the method comprising:
   (a) positioning a catheter at a treatment site in the patient's vasculature;
   (b) performing a clot dissolution treatment procedure at the treatment site, wherein the clot dissolution treatment procedure comprises delivering ultrasonic energy and a therapeutic compound from the catheter to the treatment site;
   (c) delivering a thermal measurement signal from a first portion of the catheter to the treatment she during the clot dissolution treatment;
   (d) receiving the thermal measurement signal at a second portion of the catheter;

(e) comparing the delivered thermal measurement signal with the received thermal measurement signal to evaluate a blood flow rate at the treatment site; and
(f) using the blood flow rate to adjust the clot dissolution treatment.

2. The method of claim 1, further comprising repeating steps (c) and (d) a plurality of times.

3. The method of claim 2, further comprising:
creating a profile of the temperature at the treatment site during the clot dissolution treatment; and
comparing the profile with at least one reference profile to further evaluate a blood flow rate at the treatment site.

4. The method of claim 1, wherein the thermal measurement signal is delivered from an ultrasound radiating member positioned within the catheter.

5. The method of claim 4, wherein the thermal measurement signal is received at an ultrasound radiating member positioned within the catheter.

6. The method of claim 4, wherein the thermal measurement signal is received at a temperature sensor.

7. The method of claim 1, wherein the delivered thermal measurement signal is a periodic increased temperature pulse.

8. The method of claim 1, wherein the delivered thermal measurement signal is an oscillating thermal signal.

9. The method of claim 8, wherein step (e) comprises measuring the phase difference between the delivered thermal measurement signal and the received thermal measurement signal.

10. A method comprising:
positioning a catheter at a treatment site in a patient's vasculature, wherein a blockage is located at the treatment site;
performing a medical treatment at the treatment site, the medical treatment configured to reduce the blockage;
making a plurality of thermal energy measurements at the treatment site while the medical treatment is being performed;
evaluating the reduction in the blockage based on the plurality of thermal energy measurements; and
adjusting the medical treatment based on the evaluation of the reduction in the blockage.

11. The method of claim 10, wherein the catheter comprises a plurality of ultrasound radiating members and a fluid delivery lumen configured to have a cooling fluid pass therethrough.

12. The method of claim 11, wherein the plurality of thermal energy measurements are made using a thermocouple.

13. The method of claim 12, wherein the thermocouple is positioned within the fluid delivery lumen, such that the thermocouple measures the temperature of the cooling fluid passing therethrough.

14. The method of claim 10, wherein the medical treatment comprises delivering ultrasonic energy to the treatment site.

15. The method of claim 14, wherein adjusting the medical treatment comprises adjusting the position of an ultrasound radiating member relative to the blockage.

16. The method of claim 10, wherein the medical treatment comprises delivering ultrasonic energy and a therapeutic compound to the treatment site.

17. An ultrasound catheter for evaluating the efficacy of a clot dissolution treatment, the catheter comprising:
an upstream region;
a downstream region located opposite the upstream region;
a treatment zone partially extending into both the upstream region and the downstream region;
an ultrasonic assembly positioned within the treatment zone, the ultrasonic assembly comprising at least one ultrasound radiating member configured to perform a clot dissolution treatment;
a thermal energy source positioned on the catheter, the thermal energy source configured to deliver a thermal measurement signal to the treatment zone during the clot dissolution treatment;
a thermal energy detector positioned on the catheter, the thermal energy detector configured to receive the thermal measurement signal from the treatment zone;
control circuitry configured to compare the thermal measurement signal delivered from the thermal energy source to the thermal measurement signal received at the thermal energy detector, the control circuitry further comprising an algorithm for calculating a change in blood flow rate based on the comparison; and
a user interface to display the blood flow rate, whereby the clot dissolution treatment may be adjusted.

18. The catheter of claim 17, wherein the catheter further comprises a therapeutic compound delivery lumen configured to deliver a therapeutic compound to the treatment zone during the clot dissolution treatment.

19. The catheter of claim 18, wherein the thermal energy source and the thermal energy detector are positioned within the therapeutic compound delivery lumen.

20. The catheter of claim 18, wherein the thermal energy source is positioned outside the therapeutic compound delivery lumen, and the thermal energy detector is positioned within the therapeutic compound delivery lumen.

21. The catheter of claim 19, wherein the thermal measurement signal comprises a periodic pulse of increased temperature.

22. The catheter of claim 20, wherein the control circuitry is configured to compare the peak intensity of the thermal measurement signal delivered from the thermal energy source to the peak intensity of the thermal measurement signal received at the thermal energy detector.

23. The catheter of claim 17, wherein the catheter further comprises a cooling fluid lumen configured to flow a cooling fluid proximal to the ultrasonic assembly during the clot dissolution treatment.

24. The catheter of claim 23, wherein the thermal energy source and the thermal energy detector are positioned within the cooling fluid lumen.

25. The catheter of claim 24, wherein the thermal measurement signal comprises a periodic pulse of increased temperature.

26. The catheter of claim 25, wherein the control circuitry is configured to compare the peak intensity of the thermal measurement signal delivered from the thermal energy source to the peak intensity of the thermal measurement signal received at the thermal energy detector.

27. An apparatus comprising:
a catheter having an upstream region, a downstream region and a treatment zone partially extending into both the upstream region and the downstream region;
an ultrasonic assembly positioned within the treatment zone, the ultrasonic assembly comprising at least one ultrasound radiating member configured to perform a clot dissolution treatment;
a thermal energy detector positioned in the treatment zone, the thermal energy detector configured to make a plurality of thermal energy measurements during the clot dissolution treatment;

electrical circuitry for measuring thermal dilution in the treatment zone during the clot dissolution treatment; and a user interface for displaying a signal corresponding to a blood flow rate, whereby the clot dissolution treatment may be adjusted.

28. A method comprising:

positioning a catheter having an ultrasound radiating member proximal to an obstruction in a patient's vasculature;

performing an obstruction dissolution treatment by applying a therapeutic compound and ultrasonic energy to the obstruction such that the obstruction is at least partially dissolved;

sensing an at least partial reestablishment of blood flow past the partially dissolved obstruction; and adjusting the obstruction dissolution treatment in response to the at least partial reestablishment of blood flow.

29. The method of claim 28, wherein the at least partial reestablishment of blood flow is sensed by taking a plurality of thermal measurements in the patient's vasculature.

30. The method of claim 29, wherein the plurality of thermal measurements comprise introducing a thermal measurement signal into the patient's vasculature at an upstream location, receiving a the thermal measurement signal from the patient's vasculature at a downstream location, and comparing the introduced thermal measurement signal with the received thermal measurement signal.

31. The method of claim 30, wherein the introduced thermal measurement signal is a periodic increased temperature pulse.

32. The method of claim 30, wherein the introduced thermal measurement signal is an oscillating thermal signal.

33. The method of claim 32, further comprising measuring the phase difference between the introduced thermal measurement signal and the received thermal measurement signal.

34. The method of claim 28, wherein the at least partial reestablishment of blood flow is sensed by taking a plurality of acoustic measurements in the patient's vasculature.

35. The method of claim 28, wherein the at least partial reestablishment of blood flow is sensed by taking a plurality of optical measurements in the patient's vasculature.

36. A method comprising:

positioning a catheter with an ultrasound radiating member at a treatment site in a patient's vasculature, wherein a blockage is located at the treatment site;

applying ultrasonic energy at the treatment site;

making a plurality of thermal energy measurements; and determining if the ultrasound radiating member is positioned within the blockage or blood based on an evaluation of the thermal energy measurements.

37. The method of claim 36, further comprising delivering a therapeutic compound to the treatment site.

* * * * *